United States Patent [19]
Leibowitz et al.

[11] Patent Number: 5,849,484
[45] Date of Patent: Dec. 15, 1998

[54] **IN VITRO ASSAY FOR INHIBITORS OF THE INTRON SELF-SPLICING REACTION IN *PNEUMOCYSTIS CARINII***

[75] Inventors: Michael J. Leibowitz, Manalpan; Yong Liu, Piscataway, both of N.J.

[73] Assignee: University of Medicine & Dentistry of NJ, Piscataway, N.J.

[21] Appl. No.: 491,690

[22] Filed: Jun. 19, 1995

Related U.S. Application Data

[63] Continuation of Ser. No. 68,248, May 27, 1993, abandoned, which is a continuation-in-part of Ser. No. 922,987, Jul. 30, 1992, abandoned.

[51] Int. Cl.$^6$ .............................. C12Q 1/68; C12P 19/34; C07H 21/04

[52] U.S. Cl. ..................... 435/6; 435/91.21; 435/91.5; 435/91.51; 435/91.53; 435/184; 435/195; 536/24.33; 935/8; 935/78; 935/17; 935/18

[58] Field of Search ................. 435/6, 91.53, 91.21, 435/91.5, 91.51, 184; 536/24.33; 935/77, 78, 17, 18, 195, 8

[56] References Cited

PUBLICATIONS

Lin et al Gene (1992, Oct.) 119: 163–173.
Liu et al Nucleic Acids Research (1992, Jul.) 20: 3763–3772.

*Primary Examiner*—Carla J. Myers
*Attorney, Agent, or Firm*—Richard R Muccino

[57] ABSTRACT

The present invention pertains to an in vitro method for assaying for an inhibitor of the catalytic Group I self-splicing intron reaction in the nuclear rRNA genes of *Pheumocystis carinii* which comprises the steps of (a) providing a DNA template containing the intron (I) from the 26S rRNA gene in *Pneumocystis carinii* and a portion of the 5' and 3' flanking exons (E1 and E2, respectively) between nucleotides 1963 and 2267 of 26S rRNA (660 nucleotides of amplified rRNA gene including the group I intron); (b) preparing an RNA precursor by transcription of the DNA template in the presence of labeled nucleoside triphosphates to produce a labeled RNA precursor (E1-I-E2); (c) purifying the RNA precursor; (d) incubating the RNA precursor and the inhibitor in the presence of guanosine triphosphate and magnesium ions; and (e) determining the degree of inhibition by the inhibitor on the intron splicing reaction in the RNA precursor by measuring the amount of labeled splicing intermediates and splicing products.

18 Claims, 27 Drawing Sheets

FIGURE 2A

```
cgaaagagag gaggtagcac tgTTCCGTAG GTGAACCTGC GGAAGGATCA
TTAatgaaat gttgtcaaga actagtttat ctggttcttg acattttcat    100
cataacactt gtgaacatta aagatttgct ttgacaggat gggagttagc
tttcgtcctg tcagaggttt tcaattaaaa cttttttggt gtttcggtta    200
aaaatataat ttttaaAAAC TTTCAGCAAT GGATCTCTTG GTTCCCGCGT
CGATGAAGAA CGTGGCAAAA TGCGATAAGT AGTGTGAATT GCAGAATTCA    300
GTGACTCATC GAATTTTTGA ACGCATATTG CGCTCCTCAG TATTCTGTGG
AGCATGCCTG TTTGAGCGTC ATTTttatac ttgaaccttt ttaaggtttg    400
tgttgggcta tgcattttag tattttttaca agatgctagt ctaaaatgga
atccagaata ttatttcgtg cagcgtaata gggttaaatt ccaattcgct    500
gtttttagaa atgatagact ggtttgtcta ttgttcctag agagcaattt
ttgaacCTTT GACCTCAAAT CAGGTAGGAT TACCCGCTGA ACTTAAGCAT    600
ATCAATAAGC GGAGGAAAAG AAACTAACAA GGATTCCCTC AGTAACGGCG
AGTGAAGTGG GAAAAGCTCA AAATTAAAAT CTGGCGAGGA TCCTCGTCCG    700
AGTTGTAATT TAGAGAAGTG CTTTTGGCTT GATGCTCTAT TTAAAGTCCT
TTGGAACAAG GCATCATAGA GGGTGATAAT CCCGTACGAG TAGGGTTATT    800
AAGCTATGTA AAGCACATT  CGAAGAGTCG AGTTGTTTGG GATTGCAGCT
CAAAATGGGT GGTAAATTTC ATCTAAAGCT AAATATTAGC GGGAGACCGA    900
TAGCGAACAA GTAGAGTGAT CGAAAGATGA AAGAACTTT  GAAAAGAGAG
TTAAATAGTA CGTGAAATTG CTGAAAGGGA AGCGCTTGCG ATCAGACATG   1000
CCTTATCAGG ATGTTGTTGT CTTGACAATA ACTATTACTT GGTTTGGCAG
GCCAACATCG GTTTCAGCTG CTAGGTAAGT GTCAAGAGAG GGTAGCCTCT   1100
TTCGTGGGGT GGTTAGCTCT TGGCTTCTGT AGTAGCAGGG ACCGGAAGGT
CTAGCGTCAG CTTGGTTGTT GGCTTAATGG TCTTAAGCGA CCCGTCTTGA   1200
AACACGGACC AAGGAGTCTA ATATCTATGC GAGTGTTTGA GTGGAAAACT
CATACGCGAA ATGAAAGTGA AGCAAAAGGT AGGAACCCTT TAAGGGTGCA   1300
CTATCGACCG GTTCAAATTT ATTTGGATTG AGTAAGAGCA TAGCTATTGG
GACCCGAAAG ATGGTGAACT ATGCCTGAAT AGGGTGAAGC CAGAGGAAAC   1400
TCTGGTGGAG GCTCGTAGCG GTTCTGACGT GCAAATCGAT CGTCAAATTT
GGGCATAGGG GCGAAAGACT AATCGAACCA TCTAGTAGCT GGTTCCTGCC   1500
GAAGTTTCCC TCAGGATAGC AGAAACTCAA TATCAGTTTT ATGAGGTAAA
GCGAATGATT AGAGGCATTG GGGTTGAAAC AACCTTAACC TATTCTCAAA   1600
CTTTAAATAT GTAAGAAGTC CTTGTTGCTT AATTGAACAT GGACATTAGA
ATGAGAGTTT CTAGTGGGCC ATTTTTGGTA AGCAGAACTG GCGATGCGGG   1700
ATGAACCGAA CGCGAGGTTA AGGTGCCGGA AGCACGCTCA TCAGATACCA
CAAAAGGTGT TAGTTCATCT AGACAGTAGG ACGGTGGCCA TGGAAGTCGG   1800
AATCCGCTAA GGAGTGTGTA ACAACTCACC TACCGAATGA ACTGGCCCTG
AAAATGGATG GCGCTCAAGC GTGCTACCTA TACCTCGCCG TCTGGGATAA   1900
TGATTCCTAG ACGAGTAGGC AGGCGTGGGG GTCGTGGCGA AGCCTAGGGC
GTGAGCCCGG GTTGAACGGC CTCTAGTGCA GATCTTGGTG GTAGTAGCAA   2000
```

FIGURE 2B

```
ATATTCAAAT GAGGACTTTG AAGACTGAAG TGGGGAAAGG TTCCATGCGA
ACAGTTATTG GGCATGGGTT AGTCGATCCT AAGAGATAGG GAAACTCCGT      2100
TTTAAAGTGC GCGATTTTTC GCGCCTCTAT CGAAAGGGAA TCCGGTTAAT
ATTCCGGAAC CAGGATATGG ATTCTTCACG GCAACGTAAA TGAAGTCGGA      2200
GACGTCAGCG GGGGCCTGG  GAAGAGTTAT CTTTTCTTCT TAACAGCCTA
TCACCCTGGA ATCGGTTTAT CCGGAGATAG GGTTCAATGG CTGGTAGAGT      2300
TCAGCACTTC TGTTGAATCC AGTGCGCTTT CGATGACCCT TGAAAATCCG
ACGGAAGGAA TAGTTTTCAT GCCTGGTCGT ACTCATAACC GCAACAGGTC      2400
TCCAAGGTGA ACAGCCTCTA GTTGATAGAA TAATGTAGAT AAGGGAAGTC
GGCAAAATAG ATCCGTAACT TCGGGATAAG GATTGGCTCT AAGGATTGGG      2500
TGCATTGGGC TTTAATCGGA AGCTATTGGA CCAGACGGGA ACTACCTTGG
GAAACCGAGG CGGATCCTGT TAGGATCGAT CAGTGAATGA TTTTAGCAGC      2600
CCTTTGGGCG TCCGATGCAC GCTTAACAAT CAACTTAGAA CTGGTACGGA
CAAGGGGAAT CTGACTGTCT AATTAAAACA TAGCATTGCG ATGGCCAGAA      2700
AGTGGTGTTG ACGCGATGTG ATTTCTGCCC AGTGCTCTGA ATGTCAAAGT
GAAGAAATTC AACCAAGCGC GGGTAAACGG CGGGAGTAAC TATGACTcac      2800
cttttgaggg tcatgaaagc ggcgcgaaag tgttagctag tgatccgaaa
aataaattcg ggttgcgaca ctgtcaaatt gcggggagtc cctaaagatt      2900
caactactaa gcagcttgtg gaaacacagt tgtggccgag ttaatagccc
tgggtatagt aacaatgttg aatatgactc ttaattgagg aaatgggtga      3000
tccgcagcca aatcctaagg acattttatt gtctatggat gcagttcagc
gactagacgg cagtgggtat tgtagagata tggggttatt tatggcctta      3100
tctacaatgc ttaaggtata gtctaatctc tttcgaaaga aagagtagtg
tgCTCTTAAG GTAGCCAAAT GCCTCGTCAT CTGATTAGTG ACGCGCATGA      3200
ATGGATTAAC GAGATTCCCA CTGTCCCTAT CTACGATCTA GCGAAACCAC
AGCCAAGGGA ATGGGCTTGG CAAAATCAGC GGGGAAAGAA GACCCTGTTG      3300
AGCTTGACTC TAGTTTGACA TTGTGAAAAG ACATAGAGGA TGTAGAATAG
GTGGGAGCTT CGGCGCCTGT GAAATACCAC CGCCTTTATT GTTTTTTTAC      3400
TTAATCAGTG GAGCGGGACT GAGCTTTTGC TCATCTTTTA GCGTTAAGGT
CCTTTTACGG GCCGACCCGA GTTGATGACA TTGTCAGATG GGGAGTTTGG      3500
CTGGGGCGGC ACATCTGTCA AAAGATAACG CAGGTGTCCT AAGGGGAGCT
CATTGAGAAC AGAAATCTCA AGTAGAATAA AAGGGTAAAA GTTCCCTTGA      3600
TTTTGATTTT CAGTACGAAT ACAAACCATG AAAGTGTGGC CTATCGATCC
TCTAAATCCT CGAAATTTGA GGCTAGGGGT GCCAGAAAAG TTACCACAGG      3700
GATAACTGGC TTGTGGCAGC CAAGCGTTCA TAGCGACGTT GCTTTTTGAT
CCTTCGATGT CGGCTCTTCC TATCATACCG AAGCAGAATT CGGTAAGCGT      3800
TGGATTGTTC ACCCACTAAT AGGGAACGTG AGCTGGGTTT AGACCGTCGT
GAGACAGGTT AGTTTTACCC TGCTGATGAA GTTATCGCAA TGGTAATTCA      3900
GCTTAGTACG AGAGGAACCG TTGATTCAGA TATTTGGTTT TTGCGGTTGT
CTGACCAGGC AGTGCCGCGA AGCTATCATC TGTTGGATTA TGGCTGAAAG      4000
```

FIGURE 2C

```
CCTCTAAGTC AGAATCCATG CCAGAAAGCG ATGATATTTC CTCACGTTTT
TTGATACAAA TAGGCATCTT GCCAATATCA GTATTTGGAC GGGTGGAGGC    4100
GGACGGAAGT GTTCGTCTCT GTCCATTAAT ATTAATTAAT ATTCGTGAGG
GCGAATCCTT TGTAGACGAC TTAGTTGAGG AACGGGGTAT TGTAAGCAGT    4200
AGAGTAGCCT TGTTGTTACG ATCTGCTGAG ATTAAGCCtt tgttcccaag
atttgt   4256
```

FIGURE 3

```
Pc  taaAAACTTT  CAGCAATGGA  TCTCTTGGTT  CCCGCGTCGA  TGAAGAACGT
Sc  ---.......  ..A...C...  ..........  .T...A....  .........C
Tp  AGA.......  ..A.GG....  .A........  ....T.A...  .........C
Hs  ---CG...C.  T...GG....  ..A..C..C.  .GT.......  .........C Pc  GGCA--AAAT  GCGATAAGTA  GTGTGAATTG  CAGAATTCAG  TGACTCATCG  95
Sc  A..G--....  ......C...  A.........  ........C.  ...A......  95
Tp  A..G--....  ......C...  A..C......  ......--.C. C..G...A.A  96
Hs  A..GCT.GC.  ....G..T..  A.........  ...G.CA..T  ...-......  96

Pc  AATTTTTGAA  CGCATATTGC  GCTCCTCAGT  ATTCTGTGGA  GCATGCCTGT
Sc  ...C......  ....C.....  ..C...TG..  ....CAG..G  ..........
Tp  G..C......  A...AG.G.T  .GAGG.GTAA  .AA.CT.CAT  .TT..TA.TA
Hs  .CAC..C...  ....CT.GCG  ..C..GGGT.  CC..CCG..G  CT.C......

Pc  TTGAGCGTCA  TTT  158
Sc  ..........  ...  158
Tp  G..T.GCA--  ---  154
Hs  C........G  C..  159
```

FIGURE 5A

```
Pc CTTTGACCTC AAATCAGGTA GGATTACCCG CTGAACTTAA GCATATCAAT
Sc G.........  .......... ...G......  ..........  ..........
Tp --C.ACA.CT G.TA..A.C. A.........  ..........  ........G.

Pc AAGCGGAGGA AAAGAAACTA ACAAGGATTC CCTCAGTAAC GGCGAGTGAA   100
Sc .......... ........C. ...-C.....G ...T......  ..........    99
Tp .......... .......... ..T.....AG ..C......T .....A....    98

Pc GTGGGAAAAG CTCAAAATTA AAATCTGGCG AGGATCCTCG TCCGAGTTGT
Sc .C..C..... ......T..G ........-T .CCT..GGT. C.........
Tp CA..CT.... ......G.G. ........AA .--------- -.A...A....

Pc AATTTAGAGA AGTGCTTTTG GCTTGATGCT CTATTTAAAG TCCTTTGGAA   200
Sc .....G.... G.GCAAC..T .GGGCCGTTC ..TG.CT.T. .T.C......   198
Tp ...C..A... GT.AACCCAA AGC.A.GCTC ..CGCAT... .T.C......   188

Pc CAAGGCATCA TAGAGGGTGA TAATCCCGTA CGAGTAGGGT TATTAAGCTA
Sc ..G.A.G... .......... GC.......G T.GCG...AG .GCGGTT..T
Tp ..G.A.G... A......... C..C...... GTC.GT.A.G A..GCT.G.G

Pc TGTAAAAGCA CATTCGAAGA GTCGAGTTGT TTGGGATTGC AGCTCAAAAT   300
Sc ...-....TG .C........ .......... ......A... .....T..G.   297
Tp AAGGG...-G .-...A.... ....G..... .......... ...C.T..G.   286

Pc GGGTGGTAAA TTTCATCTAA AGCTAAATAT TAGCGGGAGA CCGATAGCGA
Sc .......... ..C....... .......... .G...A.... ..........
Tp ...A.A.... C...T..... .......... ACA....... ..........

Pc ACAAGTAGAG TGATCGAAAG ATGAAAAGAA CTTTGAAAAG AGAGTTAAAT   400
Sc .......C.. ....G..... .......... .......... .....G...A   397
Tp .......CT. C..AG..... .......... .......... ..G......-   385

Pc AGTACGTGAA ATTGCTGAAA GGGAAGCGCT TG-------- CGATCAGACA
Sc .......... ....T..... ......G..A .T-------- T.........
Tp ..-..T.... .CC.T...G. A......TG. A.AAGAGCAA TA.A.T.GAC

Pc TGCCTTATCA GG--ATGTTG TTGTCTTGAC AATAACTATT ACTTGGTTTG   490
Sc ..GTG.T.TG T.CCC.C.GC .CC.TG..GG T.GGGA...C T.GCAT..CA   489
Tp G..GCATAAG ..GG.A..GT .AC..ACTG. GGAGT.G..A CGAAA.G.C.   484
```

FIGURE 5B

```
Pc GCAGGCCAAC A--------- ---------- TCGGTTTCAG CTGCTAGGTA
Sc CTG.....G. .--------- ---------- ..A....TG. TG..AG.A..
Tp ATGA.TA.GG .AAGGACACA GAACTTCTAC G.C.G.CAGA AGA.A.AA.G

Pc AGTGTCAAGA GAGGGTAGCC TCTTTCGTGG GGTGGTTAGC TCTTGGCTTC   571
Sc .A.CCAT..G A.T.TAGCTT G.C.CG..AA .TATTA.... CTG...GAAT   570
Tp ...TCAG.TT ..A..-..T. A.C.GA.ATC ..G...C.AA C.AGAT.AAA  583

Pc TGTAGTAGCA GGGACCGGAA GGTCTAGCGT CAG-CTTGGT TGTTGGCTTA
Sc AC.GCC...T .....T.AGG AC.GCGA... A..T.AA..A ..C.....A..
Tp A.GGAA.CTT CA...T...C T.AGGG..C. A..--GGC.A .T...T.AA.

Pc ATGGTCTTAA GCGACCCGTC TTGAAACACG GACCAAGGAG TCTAATATCT   670
Sc .....TA..T ..CG...... .......... .......... .....CG...   670
Tp ....CT.CT. CT........ .......... .......... ....TC.AT.   681

Pc ATGCGAGTGT TTGAGTGGA- AAACTCATAC GCGAAATGAA AGTGAAGCAA
Sc .......... ...G...T.- ....C..... ...T...... .......-.GT
Tp .A........A .A.G.....G ....C.G.C. .......C... .....GTAC.

Pc AAGGTAGGAA CCCTTTAAGG GTGCACTATC GACCGGTTCA AATT-TATTT   768
Sc .G.T.G..GC .T.GCA.GA. ......A... .....A.C.T G..G-.C..C   767
Tp .G.T--.CC. AG.CGC.... TA...GC... AC...ACCT. G...C.CCGA   779

Pc GGA-----TT GAGTAAGAGC ATAGCTATTG GGACCCGAAA GATGGTGAAC
Sc ...TGGAT.. .......... ......G... .......... ..........
Tp A..AGGGT.C ...G...... T..AT.G..A .......... ..........

Pc TATGCCTGAA TAGGGTGAAG CCAGAGGAAA CTCTGGTGGA GGCTCGTAGC   863
Sc .......... .......... .......... .......... ..........   867
Tp ..C..T.... .......... .....G.... .......... A.........   879

Pc GGTTCTGACG TGCAAATCGA TCGTCAAATT TGGGCATAGG GGCGAAAGAC
Sc .......... .......... .....G.... ....T..... ..........
Tp .A.A...... .........T .......... ..A.TG.... ..........

Pc TAATCGAACC ATCTAGTAGC TGGTTCCTGC CGAAGTTTCC CTCAGGATAG   963
Sc .......... .......... .......... .......... ..........   967
Tp .......... .......... .......CT. .........T ..........   979
```

FIGURE 5C

```
Pc CAGAAACTCA ATATCAGTTT TATGAGGTAA AGCGAATGAT TAGAGGCATT
Sc .....G...- G......... .......... .......... ......TTCC
Tp ..AG.G.AAG TACG...... ...T...... .......... ......AC.C

Pc GGGGTTGAAA CAACCTTAAC CTATTCTCAA ACTTTAAATA TGTAAGA--A 1061
Sc .....C.... TG.....G.. .......... .......... ........--. 1064
Tp ......CC.. G..T..CG.. .......... .........T G......GCC 1079

Pc GTCCTTGTTG CTTAATTGAA CATGGACATT AGAATG-AGA GTTTCTAGTG
Sc .........A .......... .G........ T.....A... .C..T.....
Tp .CGGAGT..T .......... .-.CTCGGG. ......C..T .C.CT.....

Pc GGCCATTTTT GGTAAGCAGA ACTGGCGATG CGGGATGAAC CGAACGCGAG 1160
Sc .......... .......... .......... .......... ......TAGA 1164
Tp .......... .......... .......... A......... .T....TTGA 1175

Pc GTTAAGGTGC CGGAA-GCAC GCTCATCAGA TACCACAAAA GGTGTTAGTT
Sc .......... .....TA... .......... C......... ..........
Tp .A.....C.. .CA..T.... .......... .......... ......G...

Pc CATCTAGACA GTAGGACGGT GGCCATGGAA GTCGGAATCC GCTAAGGAGT 1259
Sc .......... .CC....... .......... .......... .......... 1264
Tp ...A.G.... .C........ ...T...... ..TA...... .......... 1278

Pc GTGTAACAAC TCACCTACCG AATGAACTGG CCCTGAAAAT GGATGGCGCT
Sc .......... .....GG... ........A. .......... ..........
Tp .......... ......G... ........A. .......... ..........

Pc CAAGCGTGCT ACCTATACCT CGCCGTCTGG GAT--AATGA TTCCTAGACG 1357
Sc ........T. ........TC TA.....A.. .T.GAT.... .G..CT.... 1364
Tp G.......T. G..G....TC AA...A..A.A .CAAATGC.. GG.T.T..T. 1378

Pc AGTAGGCAGG CGTGGGGGTC -GTGGCGAAG CCTAGGGCGT GAGCCCGGGT
Sc .......... .....A.... A...A..... .....AC... A..GT.....
Tp ......AG.. ....ATC..T -.CCTA.... TA.T...... ....T-ATA

Pc TGAACGGCCT CTAGTGCAGA TCTTGGTGGT AGTAGCAAAT ATTCAAATGA 1456
Sc C......... .......... .......... .......... .......... 1464
Tp G..G.A..GA T......... .......... .......... .......... 1476
```

FIGURE 5D

```
Pc GGACTTTGAA GACTGAAGTG GGGAAAGGTT CCATGCGAAC AGTTATTGGG
Sc .A........ .......... .......... ...C.TC... ..CAG....A
Tp .A........ ...C...... .A...G.... .....A.... ..CA....TT

Pc CATGGGTTAG TCGATCCTAA GAGATAGGGA AACTCCGTTT TA-AAGTGC- 1554
Sc .G........ .......... .....G.... .G........ C.-...GC.T 1563
Tp ..........C .......... ..C.....TT ......T.GC A.T.CAA.AA 1576

Pc GCGATTTTTC GCGCCTCTAT CGAAAGGGAA TCCGGTTAAT ATTCCGGAAC
Sc .ATT..A.G. AG...A.C.. .......... ......-...G ..........
Tp .ACG..C.CG TTTT.GT.G. .A........ .GA....... .....TC..G

Pc CAGGATATGG ATTCTTCACG GCAACGTAAA TGAAGTCGGA GACGTCAGCG 1654
Sc TT........ .......... .T.......C ....TGT... ......G... 1662
Tp .T...CG... -.ATAGAGT. .T...AC... GA..CC.... ..........A 1675

Pc GGGGGCCTGG GAAGAGTTAT CTTTTCTTCT TAACAGCCTA TCACCCTGGA
Sc C.A.C..... ..G....... .......... .......T.. ......C...
Tp ..A.C.ACT. .......... ........T. ......TA... .GG...A..A.

Pc ATCGGTTTAT CCGGAGATA- GGGTTCAATG GCTGGTAGAG TTCAGCA-CT 1752
Sc ..T....... ........G- ....CTT... .....A.... GC.....-.C 1760
Tp .AT..A.... ..A......T C..C.GT.C. TA...C.... CAGCT..C.C 1775

Pc TCTGTTGAAT CCAGTGCGCT TTCGATGACC CTTGAAAATC CGACGGAAGG
Sc .T..C..GC. ...G...... .GT..C.G.. .G........ .ACA......
Tp .AA.AGCTG. .AGT...... .CT....... .......... T.GG...--.

Pc AATAGTTTTC ATGCCTGGTC GTACTCATAA CCGCAACAGG TCTCCAAGGT 1852
Sc .......... ....TA.... .....G.... .....G.... .......... 1860
Tp .CATAA.... .C...A.T.. ....C..... .....T.... .......... 1873

Pc GAACAGCCTC TAGTTGATAG AATAATGTAG ATAAGGGAAG TCGGCAAAAT
Sc .......... .......... .......... .......... ..........
Tp T.G....... .G..CC.... ..C....... .......... .........T.

Pc AGATCCGTAA CTTCGGGATA AGGATTGGCT CTAAGGATTG GGTGCATTGG 1952
Sc .......... .......... .......... ......G.C. ...AGTGA.. 1960
Tp G......... .......... .......... ..G.....C. ...AT.AA.. 1973
```

FIGURE 5E

```
Pc GCTTTAATCG GAAGCTATTG GACCAGACGG GAACTACCTT GGGAAAC---
Sc ..C..GG..A ..C..AGCG. .CGTGCTT.T .G...G.T.G .T.GGG.TTG
Tp C.A...GAT. AT.T.C.AGC TTGTTTGTTA .TGTGG.AAC AT.-------

Pc -----CGAGG CGGATCCTGT TAGGATCGAT CAGTGAATGA TTTTAGCAGC 2044
Sc CTCTG.T... ....CTACT. GC.TGC.TTG TT..AG.C.G CC..G.T..G 2060
Tp ---------- ----CTGATA G.CTTG...C .GAA....TC ..G.G.T..A 2052

Pc CCTTTGGGCG TCCGATGCAC GC------TT AACAATCAAC TTAGAACTGG
Sc T..C.T.TA. A...TC..TT ..TACAAT.A .CAG...... ..........
Tp ...------- -.G.TC.TCT TTATACAA.. ...G...... .C.......A

Pc TACGGACAAG GGGAATCTGA CTGTCTAATT AAAACATAGC ATTGCGATGG 2138
Sc .......... .......... .......... .......... .......... 2160
Tp AG......A ..T....C.. ....T....A ......A... ....T..C.. 2144

Pc CCAGAAAGTG GTGTTGACGC GATGTGATTT CTGCCCAGTG CTCTGAATGT
Sc T......... A......... A......... .......... ..........
Tp ..-TC..CA. ...A....A. A......... .......... ..........

Pc CAAAGTGAAG AAATTCAACC AAGCGCGGGT AAACGGCGGG AGTAACTATG 2238
Sc .......... .......... ......A.. .......... .......... 2260
Tp ........C. C......... .......... .......... .......... 2243

Pc ACTCTCTTAA GGTAGCCAAA TGCCTCGTCA TCTGATTAGT GACGCGCATG
Sc .......... .......... .......... ...A...... ..........
Tp .......... .......... .......... ...A...... ..........

Pc AATGGATTAA CGAGATTCCC ACTGTCCCTA TCTACGATCT AGCGAAACCA 2338
Sc .......... .......... .......... .....T.... .......... 2360
Tp .......... T......A.. .......... .....T.... ......C... 2343

Pc CAGCCAAGGG AATGGGCTTG GCAAAATCAG CGGGGAAAGA AGACCCTGTT
Sc .......... ..C....... ...G...... .......... ..........
Tp ....T..... ..C......A .A.T...... .......... ..........

Pc GAGCTTGACT CTAGTTTGAC ATTGTGAAAA GACATAGAGG ATGTAGAATA 2438
Sc .......... .......... ........G. .......... G......... 2460
Tp .......... .....C.A.. T........T .G..CGTG.. G.A...CC.. 2443
```

FIGURE 5F

```
Pc GGTGGGAGCT TCGGCGCCTG TGAAATACCA CCGCCTTTAT TGTTTTTTTA
Sc A.........  .........A. .......... .TA....... A....C....
Tp ........AG AAAT..AGCC ..T..A.... .TA..CACG. A...CA....G

Pc CTTAATCAGT GGAGCGGGAC TGAGCTT--T TGCTCATCTT TTAGCGTT-A 2535
Sc ....T...A. .A.....AG. ...GAA..CA. .TTC..CG.. C....A..C. 2560
Tp ....T.TC.. .A..-----A AA.AAC.GG. GAGAACCAG. .CTAAAA.T. 2538

Pc AGGTCCTTTT ACGGGCCGAC CCGAGTTGAT GACATTGTCA GATGGGGAGT
Sc ......CA.. CG....T..T ...G.....A .......... .G........
Tp ...A.A...A TT.TCTGATT TTTGCGAA.A .....G..T. .GG.......

Pc TTGGCTGGGG CGGCACATCT GTCAAAAGAT AACGCAGGTG TCCTAAGGGG 2635
Sc .......... .......... ..T...C... .......A.. .......... 2660
Tp ...T...... ...A.TGC.. ..T...CC.. ........C. .......T.T 2638

Pc AGCTCATTGA GAACAGAAAT CTCAAGTAGA ATAAAAGGGT AAAAGTTCCC
Sc G......G.. .......... ...C...... .C........ ...---G...
Tp ......G... ....G..... ....C..... .C........ ....C.A.A

Pc TTGATTTTGA TTTTCAGTAC GAATACAAAC CA-TGAAAGT GTGGCCTATC 2734
Sc C.T.G..... -.......GT .......... ..T....... .......... 2756
Tp .......... ..........T .......... .G-C.....C .......... 2737

Pc GATCCTCTAA ATCCTCGAAA TTTGAGGCTA GGGGTGCCAG AAAAGTTACC
Sc ......T..G TC.....G.. .......... .A........ ..........
Tp ......T... -CTT.AC..G ...T.A.... .A....T... ..........

Pc ACAGGGATAA CTGGCTTGTG GCAGCCAAGC GTTCATAGCG ACGTTGCTTT 2834
Sc .......... .......... ....T..... .......... ..A....... 2856
Tp .......... .......... .........A ........T.. .......... 2836

Pc TTGATCCTTC GATGTCGGCT CTTCCTATCA TACCGAAGCA GAATTCGGTA
Sc .....T.... .......... .......... .......... ..........
Tp .......... .......... .......... .TGT...... ......ACA.

Pc AGCGTTGGAT TGTTCACCCA CTAATAGGGA ACGTGAGCTG GGTTTAGACC 2934
Sc .......... .......... .......... ...A...... .......... 2956
Tp C.T..C.... .........G .......... .......... .......... 2936
```

FIGURE 5G

```
Pc GTCGTGAGAC AGGTTAGTTT TACCCTGCTG ATGAAGTTAT C--GCAATGG
Sc .......... .......... ......A... .....TG.TA .CA.....A.
Tp .......... .......... ......A... .....ACG.. GTT..G.CA.

Pc TAATTCAGCT TAGTACGAGA GGAACCGTTG ATTCAGATAT TTGGTTTTTG 3032
Sc .....G.A.. .......... .....A...C ....G....A .......... 3056
Tp .....T.AG. .......... ......C..A .A........A .....AAA.A 3036

Pc CGGTTGTCTG ACCAGGCAGT GCCGCGAAGC TATCATCTGT TGGATTATGG
Sc ...C...... .T......T. .......... -.C....C.C ..........
Tp .......... .AA..A...A ....T..... ..C....... ..........A

Pc CTGAAAGCCT CTAAGTCAGA ATCCATGCCA GAAAGCGATG ATATTT---- 3128
Sc .....C.... .......... ........T. ...C...G.. ..T.C.TTGC 3155
Tp .....G.... .......... ........TG ......A... TCTAAGTGTG 3136

Pc ----CCTCAC GTTTTTTGAT ACAAAT-AGG CATCTT---- ---------G
Sc TCCA.ACA.T A.AGA.G... ..G...A... .G..C.TGTG GCGTCGCTGA
Tp ATGATAAACG AAAAAAAATA .G....---- ---------- ----------

Pc CCAATATCAG TATTTGGACG GGTGGAGGCG GACGGAAGTG TTCGTCTCTG 3210
Sc A.C...G... GC.AGCA... .TGCACTTG. CGGAA.G.CC ..G.GTG..T 3255
Tp ----..AGTT CGAAA..TA. A.C....AA. AG..A..AA. C.T.ATCT.A 3208

Pc TCCATTAATA TTAATT---A ATATTCGTGA GGGCGAATCC TTTGTAGACG
Sc G.TGGCG.AT .GC.A.GTC. T.T.G....G ..ATA....A ......T...
Tp A.TGC....C G.....CCA. ..TA..A.CT AC.TA....T ..........

Pc ACTTAGTTGA GGAACGGGGT ATTGTAAGCA GTAGAGTAGC CTTGTTGTTA 3307
Sc ......A..T AC........ .........G .......... .......... 3355
Tp .....A.--. C.G.AC.... ........T. TG.......A A.--A.TC.. 3304

Pc CGATCTGCTG AGATTAAGCC tttgttccca agatttgt     3345
Sc .......... .......... ......GT.T -.......    3392
Tp .......... .....C.... CG.C.C.TT. -......A.   3341
```

FIGURE 7

```
Pc1   GGTTTGGCAG GCCAACA--- ---------- ------TCGG TTTCAGCTGC TAGGTAAGTG  525
Pc2   .......... ....... --- ---------- ------.... .......... .......AGA
Sc    AT..CACTG. ....G..--- ---------- ------..A. ...TG.TG.. AG.A...A.C
Tp    A.G.C.ATGA .TA.GG.AAG GACACAGAAC TTCTACG.C. G.CAGAAGA. A.AA.G...T

Pc1   TCAAGAGAGG GTAGCCTCTT TCGTGGGGTG GTTAGCTCTT GGCTTCTGTA GTAGCAGGGA  585
Pc2   ........A. .......... .TT....... T......... .AT.GTA... .C...T....
Sc    CAT..GA.T. TAGCTTG.C. CG...AA.TAT TA....CTG. ...GAATAC.G CC...T....
Tp    CAG.TT..A. .-...T.A.C. GA.ATC..G. ...C.AAC.AG AT.AAAA.GG AA.CTTCA..

Pc1   CCGGAAGGTC TAGCGTC--- -AG-CTTGGT TGTTGGCTTA ATGGTCTTAA GCGACCCGTC  640
Pc2   .......... ....AAAATA T..-...... .......... .......... ..........
Sc    .T.AGGAC.G CGA...A--- -..T.AA..A ..C....A.. .....TA..T ..CG......
Tp    .T...CT.AG GG..C.A--- -..--GGC.A .T...T.AA. ....CT.CT. CT........

Pc1   TTGAAACACG GACCAAGGAG TCTAATATCT ATGCGAGTGT TTGAGTGGA- AAACTCATAC  699
Pc2   .......... .......... .......... .......... ...G.....- ....C...G.
Sc    .......... .......... .....CG... .......... ...G...T.- ....C.....
Tp    .......... .......... ....TC.AT. .A........A .A.G.....G ....C.G.C.

Pc1   GCGAAATGAA AGTGAAGCAA AAGGTAGGAA CCCTTTAAGG GTGCACTATC GACCGGTTCA  759
Pc2   .......... .......... .-...G.... .....C-G.. ......C... ..........
Sc    ...T...... .......-.GT .G.T.G..GC .T.GCA.GA. ......A... ......A.C.T
Tp    ......C... .....GTAC. .-...GCC.. G..G-C.... TA...GC... AC...ACCT.

Pc1   AATT-TATTT GGA-----TT GAGTAAGAGC ATAGCTATTG GGACCCGAAA GATGGTGAAC  813
Pc2   ....-..... ...-----.C .....G.... .......... .......... ..........
Sc    G..G-.C..C ...TGGAT.. .......... ......G... .......... ..........
Tp    G...C.CCGA A..AGGGT.C ...G...... T..AT.G..A .......... ..........

Pc1   TATGCCTGAA TAGGGTGAAG CCAGAGGAAA CTCTGGTGGA GGCTCGTAGC GGTTCTGACG  873
Pc2   .......... .......... .......... .......... .......... ..........
Sc    .......... .......... .......... .......... .......... ..........
Tp    ..C..T.... .......... .....G.... .......... A......... .A.A......

Pc1   TGCAAATCGA TCGTCAAATT TGGGCATAGG GGCGAAAGAC TAATCGAACC ATCTAGTAGC  933
Pc2   .......... .......... .......... .......... .......... ..........
Sc    .......... .....G.... ....T..... .......... .......... ..........
Tp    .........T .......... ..A.TG.... .......... .......... ..........

Pc1   TGGTTCCTGC CGAAGTTTCC CTCAGGATAG C  964
Pc2   .......... .......... .......... .
Sc    .......... .......... .......... .
Tp    .......CT. ..........T .......... .
```

FIGURE 8

```
Pc1 GGGAACGTGA GCTGGGTTTA GACCGTCGTG AGACAGGTTA GTTTTACCCT GCTGATGAAG 2970
Pc2 .......... .......... .......... .......... .......... ..........
Sc  ......A... .......... .......... .......... .......... A........T
Tp  .......... .......... .......... .......... .......... A........A

Pc1 TTATC--GCA ATGGTAATTC AGCTTAGTAC GAGAGGAACC GTTGATTCAG ATATTTGGTT 3028
Pc2 .....--... .......... .A........ .......... .......... ..........
Sc  G.TA.CA... ..A......G .A........ ..........A ...C....G. ...A......
Tp  CG..GTT..G .CA......T .AG....... .......... C...A.A.... ...A.....A

Pc1 TTTGCGGTTG TCTGACCAGG CAGTGCCGCG AAGCTATCAT CTGTTGGATT ATGGCTGAAA 3088
Pc2 .......... .......... .......... .......... .......... .........C
Sc  .......C.. .....T.... ..T....... .....-.C... .C.C...... .........C
Tp  AA.A...... .....AA..A ...A.....T. .......C... .......... ...A.....G

Pc1 GCCTCTAAGT CAGAATCCAT GCCAGAAAGC GATGAT--AT TTCCTCAC-G TTTTTTGATA 3145
Pc2 .......... .......... .......... ......AA.. ........AC A.........
Sc  .......... .......... ..T....C.. .G....TTC. ...G...-.AC ACAA.AT.G.
Tp  .......... .......... ..TG...... A...------ --T..A.GT. .GA.GAT.A.

Pc1 CAAATAGGCA TCTTGC---- ---------- ---CAATATC AG--TATTTG GACGGGTGGA 3186
Pc2 T.G....... .T....---- ---------- ---..G.... ..TA...... .........G
Sc  TGG...C.A. .AAG..GTCC TTGTGGCGTC GCTG..CCAT ..CAGGC.A. C.AC....C.
Tp  .G..A.AAA. .AA------- ---------- ---G..AT.A ..TTCGAAA. .TA.A.C...

Pc1 GGCGGACGGA AGTGTTCGTC TCTGTCCATT A--ATATTAA --TTAATATT CGTGAGGGCG 3242
Pc2 ....A..... .......... .......... .AC...A..T --AA.....G .........T.
Sc  CTT..CG.A. ..GCC.T.GG .GCT.G.TGG CGA..TGC.. TG.C.T.T.G ....G..ATA
Tp  .AA.AG..A. .AA.C.T.-A ...TAA.TGC TAATCG.A.T TCCA...TA. .A.CTAC.TA

Pc1 AATCCTTTGT AGACGACTTA GTTGAGGAAC GGGGTATTGT AAGCAGTAGA GTAGCCTTGT 3302
Pc2 .......... .......... .......... ......C... .......... ..........
Sc  ....A..... .T........ .A..TAC... .......... ....G..... ..........
Tp  ....T..... .......... A.--.C.G.A C......... ...T.TG... ....AA.--A

Pc1 TGTTACGATC TGCTGAGATT AAGCC 3327
Pc2 .......... .......... .....
Sc  .......... .......... .....
Tp  .TC....... .......... C....
```

FIGURE 10

```
TCAAAAAGAA CATTTCTTCT GAGTGGTGAG GGGTCCGTTA GAGCACACTC
GCTCCTTGGA AGAGATGTTT TTTTTGATAT TAGGAACCAA TAGAATATTT 100
AGAATTTAAT TTAGATTAAA TTATAGAAGG GTATCTGTAG CGATAAGTTT
CCATTTCAAA TTTTTCTGAT GCAGTAGTAT GTTCTTTTCT AAAATAAAAT 200
GATAGTTTAT TAATGATTAA ACTAATTATT ATCCTTTGGC CATCTTTTTC
TACATTTTCC AGAAACAGAT CTAATTACGT TTTTGCTATC TATAATTATT 300
AAAAATAATC ATATATCTTT AAAGTTGACC TCAACGTCTT AAAATGTTTA
GTTTTTTAAT TAACCCTAAA CCCTAGAACA C                      381
```

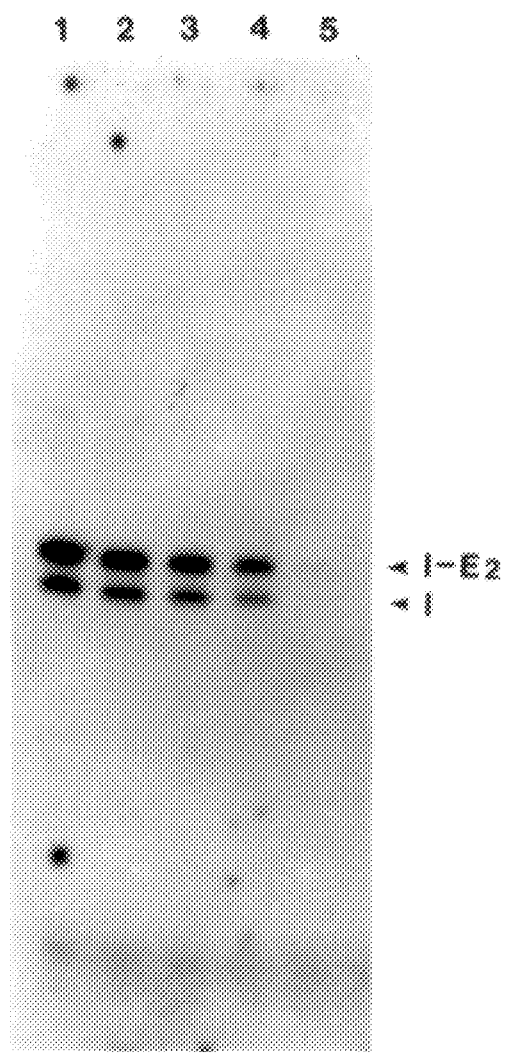

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

AACAGCTATG ACCATGAT 18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

TTCCCAGTCA CGACGTTG 18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

TGTAAAACGA CGGCCAGT 18

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

AGGGATTGGT TGGCCTGGTC CTCCGAA 27

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

CTTTCCAGTA ATAGGCTTAT CG 22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

GCTATCCTGA GGGAAACTTC GG 22

( 2 ) INFORMATION FOR SEQ ID NO:7:

( i ) SEQUENCE CHARACTERISTICS:
          ( A ) LENGTH: 24 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:7:

CCCGTCTTGA AACACGGACC AAGG                       24

( 2 ) INFORMATION FOR SEQ ID NO:8:

( i ) SEQUENCE CHARACTERISTICS:
          ( A ) LENGTH: 26 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:8:

CCCGCGATCA GCAAAAGCTA ATCTGG                     26

( 2 ) INFORMATION FOR SEQ ID NO:9:

( i ) SEQUENCE CHARACTERISTICS:
          ( A ) LENGTH: 26 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:9:

CCATACAGAA GACCATTCTT TATCCC                     26

( 2 ) INFORMATION FOR SEQ ID NO:10:

( i ) SEQUENCE CHARACTERISTICS:
          ( A ) LENGTH: 20 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:10:

GGCCGATCAA ACTCTCTTCC                           20

( 2 ) INFORMATION FOR SEQ ID NO:11:

( i ) SEQUENCE CHARACTERISTICS:
          ( A ) LENGTH: 21 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:11:

GGGAAAAGGT CGTGGGGAGC G                         21

( 2 ) INFORMATION FOR SEQ ID NO:12:

( i ) SEQUENCE CHARACTERISTICS:
          ( A ) LENGTH: 21 base pairs ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:12:

GGGGAAGACC GCCCTGATAG G        21

( 2 ) INFORMATION FOR SEQ ID NO:13:

( i ) SEQUENCE CHARACTERISTICS:
( A ) LENGTH: 26 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:13:

GAGCCAATCC TTATCCCGAA GTTACG        26

( 2 ) INFORMATION FOR SEQ ID NO:14:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:14:

GTCTAAACCC AGCTCACGTT CCC        23

( 2 ) INFORMATION FOR SEQ ID NO:15:

( i ) SEQUENCE CHARACTERISTICS:
( A ) LENGTH: 19 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:15:

GGGTGGTGGT GCATGGCCG        19

( 2 ) INFORMATION FOR SEQ ID NO:16:

( i ) SEQUENCE CHARACTERISTICS:
( A ) LENGTH: 22 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:16:

CCTTCCGCAG GTTCACCTAC GG        22

( 2 ) INFORMATION FOR SEQ ID NO:17:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:17:

CCGCAGCAGG TCTCCAAG 18

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

CGAAAGAGAG GAGGTAGCAC C 21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

GGTCCGTGTT TCAAGACGGG 20

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

GGGAACGTGA GCTGGGTTTA G 21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

GGTTTGGCAG GCCAACATCG G 21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:22:

CCATGAAAGT GTGGCCTATC G 21

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:23:

GCCTGGTCAG ACAACCGC                            18

( 2 ) INFORMATION FOR SEQ ID NO:24:

( i ) SEQUENCE CHARACTERISTICS:
    ( A ) LENGTH: 18 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:24:

GGATTATGGC TGAACGCC                            18

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:25:

GGCTTAATCT CAGCAGATCG                          20

( 2 ) INFORMATION FOR SEQ ID NO:26:

( i ) SEQUENCE CHARACTERISTICS:
    ( A ) LENGTH: 19 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:26:

GACGAGGCAT TTGGCTACC                          19

( 2 ) INFORMATION FOR SEQ ID NO:27:

( i ) SEQUENCE CHARACTERISTICS:
    ( A ) LENGTH: 18 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:27:

GTACACACCG CCCGTCGC                            18

( 2 ) INFORMATION FOR SEQ ID NO:28:

( i ) SEQUENCE CHARACTERISTICS:
    ( A ) LENGTH: 18 base pairs ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:28:

TTTAGCTCTT GATTGTAG         18

( 2 ) INFORMATION FOR SEQ ID NO:29:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:29:

CGCATATTTT ATATTATG         18

( 2 ) INFORMATION FOR SEQ ID NO:30:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:30:

GTTAGCTCTT GGCTTCTG         18

( 2 ) INFORMATION FOR SEQ ID NO:31:

( i ) SEQUENCE CHARACTERISTICS:
( A ) LENGTH: 4256 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:31:

| | | | | | | |
|---|---|---|---|---|---|---|
| CGAAAGAGAG | GAGGTAGCAC | CGTTCCGTAG | GTGAACCTGC | GGAAGGATCA | TTAATGAAAT | 60 |
| GTTGTCAAGA | ACTAGTTTAT | CTGGTTCTTG | ACATTTTCAT | CATAACACTT | GTGAACATTA | 120 |
| AAGATTTGCT | TTGACAGGAT | GGGAGTTAGC | TTTCGTCCTG | TCAGAGGTTT | TCAATTAAAA | 180 |
| CTTTTTTGGT | GTTTCGGTTA | AAAATATAAT | TTTTAAAAAC | TTTCAGCAAT | GGATCTCTTG | 240 |
| GTTCCCGCGT | CGATGAAGAA | CGTGGCAAAA | TGCGATAAGT | AGTGTGAATT | GCAGAATTCA | 300 |
| GTGACTCATC | GAATTTTTGA | ACGCATATTG | CGCTCCTCAG | TATTCTGTGG | AGCATGCCTG | 360 |
| TTTGAGCGTC | ATTTTTATAC | TTGAACCTTT | TTAAGGTTTG | TGTTGGGCTA | TGCATTTTAG | 420 |
| TATTTTTACA | AGATGCTAGT | CTAAAATGGA | ATCCAGAATA | TTATTTCGTG | CAGCGTAATA | 480 |
| GGGTTAAATT | CCAATTCGCT | GTTTTTAGAA | ATGATAGACT | GGTTTGTCTA | TTGTTCCTAG | 540 |
| AGAGCAATTT | TTGAACCTTT | GACCTCAAAT | CAGGTAGGAT | TACCCGCTGA | ACTTAAGCAT | 600 |
| ATCAATAAGC | GGAGGAAAAG | AAACTAACAA | GGATTCCCTC | AGTAACGGCG | AGTGAAGTGG | 660 |
| GAAAAGCTCA | AAATTAAAAT | CTGGCGAGGA | TCCTCGTCCG | AGTTGTAATT | TAGAGAAGTG | 720 |
| CTTTTGGCTT | GATGCTCTAT | TTAAAGTCCT | TTGGAACAAG | GCATCATAGA | GGGTGATAAT | 780 |
| CCCGTACGAG | TAGGGTTATT | AAGCTATGTA | AAAGCACATT | CGAAGAGTCG | AGTTGTTTGG | 840 |

```
GATTGCAGCT  CAAAATGGGT  GGTAAATTTC  ATCTAAAGCT  AAATATTAGC  GGGAGACCGA   900
TAGCGAACAA  GTAGAGTGAT  CGAAAGATGA  AAAGAACTTT  GAAAGAGAG   TTAAATAGTA   960
CGTGAAATTG  CTGAAAGGGA  AGCGCTTGCG  ATCAGACATG  CCTTATCAGG  ATGTTGTTGT  1020
CTTGACAATA  ACTATTACTT  GGTTTGGCAG  GCCAACATCG  GTTTCAGCTG  CTAGGTAAGT  1080
GTCAAGAGAG  GGTAGCCTCT  TTCGTGGGGT  GGTTAGCTCT  TGGCTTCTGT  AGTAGCAGGG  1140
ACCGGAAGGT  CTAGCGTCAG  CTTGGTTGTT  GGCTTAATGG  TCTTAAGCGA  CCCGTCTTGA  1200
AACACGGACC  AAGGAGTCTA  ATATCTATGC  GAGTGTTTGA  GTGGAAAACT  CATACGCGAA  1260
ATGAAAGTGA  AGCAAAAGGT  AGGAACCCTT  TAAGGGTGCA  CTATCGACCG  GTTCAAATTT  1320
ATTTGGATTG  AGTAAGAGCA  TAGCTATTGG  GACCCGAAAG  ATGGTGAACT  ATGCCTGAAT  1380
AGGGTGAAGC  CAGAGGAAAC  TCTGGTGGAG  GCTCGTAGCG  GTTCTGACGT  GCAAATCGAT  1440
CGTCAAATTT  GGGCATAGGG  GCGAAAGACT  AATCGAACCA  TCTAGTAGCT  GGTTCCTGCC  1500
GAAGTTTCCC  TCAGGATAGC  AGAAACTCAA  TATCAGTTTT  ATGAGGTAAA  GCGAATGATT  1560
AGAGGCATTG  GGGTTGAAAC  AACCTTAACC  TATTCTCAAA  CTTTAAATAT  GTAAGAAGTC  1620
CTTGTTGCTT  AATTGAACAT  GGACATTAGA  ATGAGAGTTT  CTAGTGGGCC  ATTTTGGTA   1680
AGCAGAACTG  GCGATGCGGG  ATGAACCGAA  CGCGAGGTTA  AGGTGCCGGA  AGCACGCTCA  1740
TCAGATACCA  CAAAAGGTGT  TAGTTCATCT  AGACAGTAGG  ACGGTGGCCA  TGGAAGTCGG  1800
AATCCGCTAA  GGAGTGTGTA  ACAACTCACC  TACCGAATGA  ACTGGCCCTG  AAAATGGATG  1860
GCGCTCAAGC  GTGCTACCTA  TACCTCGCCG  TCTGGGATAA  TGATTCCTAG  ACGAGTAGGC  1920
AGGCGTGGGG  GTCGTGGCGA  AGCCTAGGGC  GTGAGCCCGG  GTTGAACGGC  CTCTAGTGCA  1980
GATCTTGGTG  GTAGTAGCAA  ATATTCAAAT  GAGGACTTTG  AAGACTGAAG  TGGGAAAGG   2040
TTCCATGCGA  ACAGTTATTG  GGCATGGGTT  AGTCGATCCT  AAGAGATAGG  GAAACTCCGT  2100
TTTAAAGTGC  GCGATTTTTC  GCGCCTCTAT  CGAAAGGGAA  TCCGGTTAAT  ATTCCGGAAC  2160
CAGGATATGG  ATTCTTCACG  GCAACGTAAA  TGAAGTCGGA  GACGTCAGCG  GGGGCCTGG   2220
GAAGAGTTAT  CTTTTCTTCT  TAACAGCCTA  TCACCCTGGA  ATCGGTTTAT  CCGGAGATAG  2280
GGTTCAATGG  CTGGTAGAGT  TCAGCACTTC  TGTTGAATCC  AGTGCGCTTT  CGATGACCCT  2340
TGAAAATCCG  ACGGAAGGAA  TAGTTTTCAT  GCCTGGTCGT  ACTCATAACC  GCAACAGGTC  2400
TCCAAGGTGA  ACAGCCTCTA  GTTGATAGAA  TAATGTAGAT  AAGGGAAGTC  GGCAAAATAG  2460
ATCCGTAACT  TCGGGATAAG  GATTGGCTCT  AAGGATTGGG  TGCATTGGGC  TTTAATCGGA  2520
AGCTATTGGA  CCAGACGGGA  ACTACCTTGG  GAAACCGAGG  CGGATCCTGT  TAGGATCGAT  2580
CAGTGAATGA  TTTTAGCAGC  CCTTTGGGCG  TCCGATGCAC  GCTTAACAAT  CAACTTAGAA  2640
CTGGTACGGA  CAAGGGGAAT  CTGACTGTCT  AATTAAAACA  TAGCATTGCG  ATGGCCAGAA  2700
AGTGGTGTTG  ACGCGATGTG  ATTTCTGCCC  AGTGCTCTGA  ATGTCAAAGT  GAAGAAATTC  2760
AACCAAGCGC  GGGTAAACGG  CGGGAGTAAC  TATGACTCAC  CTTTTGAGGG  TCATGAAAGC  2820
GGCGCGAAAG  TGTTAGCTAG  TGATCCGAAA  AATAAATTCG  GGTTGCGACA  CTGTCAAATT  2880
GCGGGGAGTC  CCTAAAGATT  CAACTACTAA  GCAGCTTGTG  GAAACACAGT  TGTGGCCGAG  2940
TTAATAGCCC  TGGGTATAGT  AACAATGTTG  AATATGACTC  TTAATTGAGG  AAATGGGTGA  3000
TCCGCAGCCA  AATCCTAAGG  ACATTTTATT  GTCTATGGAT  GCAGTTCAGC  GACTAGACGG  3060
CAGTGGGTAT  TGTAGAGATA  TGGGGTTATT  TATGGCCTTA  TCTACAATGC  TTAAGGTATA  3120
GTCTAATCTC  TTTCGAAAGA  AAGAGTAGTG  TGCTCTTAAG  GTAGCCAAAT  GCCTCGTCAT  3180
CTGATTAGTG  ACGCGCATGA  ATGGATTAAC  GAGATTCCCA  CTGTCCCTAT  CTACGATCTA  3240
```

| | | | | | | |
|---|---|---|---|---|---|---|
| GCGAAACCAC | AGCCAAGGGA | ATGGGCTTGG | CAAAATCAGC | GGGGAAAGAA | GACCCTGTTG | 3300 |
| AGCTTGACTC | TAGTTTGACA | TTGTGAAAAG | ACATAGAGGA | TGTAGAATAG | GTGGGAGCTT | 3360 |
| CGGCGCCTGT | GAAATACCAC | CGCCTTTATT | GTTTTTTTAC | TTAATCAGTG | GAGCGGGACT | 3420 |
| GAGCTTTTGC | TCATCTTTTA | GCGTTAAGGT | CCTTTTACGG | GCCGACCCGA | GTTGATGACA | 3480 |
| TTGTCAGATG | GGGAGTTTGG | CTGGGGCGGC | ACATCTGTCA | AAAGATAACG | CAGGTGTCCT | 3540 |
| AAGGGGAGCT | CATTGAGAAC | AGAAATCTCA | AGTAGAATAA | AAGGGTAAAA | GTTCCCTTGA | 3600 |
| TTTTGATTTT | CAGTACGAAT | ACAAACCATG | AAAGTGTGGC | CTATCGATCC | TCTAAATCCT | 3660 |
| CGAAATTTGA | GGCTAGGGGT | GCCAGAAAAG | TTACCACAGG | GATAACTGGC | TTGTGGCAGC | 3720 |
| CAAGCGTTCA | TAGCGACGTT | GCTTTTTGAT | CCTTCGATGT | CGGCTCTTCC | TATCATACCG | 3780 |
| AAGCAGAATT | CGGTAAGCGT | TGGATTGTTC | ACCCACTAAT | AGGGAACGTG | AGCTGGGTTT | 3840 |
| AGACCGTCGT | GAGACAGGTT | AGTTTACCC | TGCTGATGAA | GTTATCGCAA | TGGTAATTCA | 3900 |
| GCTTAGTACG | AGAGGAACCG | TTGATTCAGA | TATTTGGTTT | TTGCGGTTGT | CTGACCAGGC | 3960 |
| AGTGCCGCGA | AGCTATCATC | TGTTGGATTA | TGGCTGAAAG | CCTCAAGTC | AGAATCCATG | 4020 |
| CCAGAAAGCG | ATGATATTTC | CTCACGTTTT | TTGATACAAA | TAGGCATCTT | GCCAATATCA | 4080 |
| GTATTTGGAC | GGGTGGAGGC | GGACGGAAGT | GTTCGTCTCT | GTCCATTAAT | ATTAATTAAT | 4140 |
| ATTCGTGAGG | GCGAATCCTT | TGTAGACGAC | TTAGTTGAGG | AACGGGGTAT | TGTAAGCAGT | 4200 |
| AGAGTAGCCT | TGTTGTTACG | ATCTGCTGAG | ATTAAGCCTT | TGTTCCCAAG | ATTTGT | 4256 |

( 2 ) INFORMATION FOR SEQ ID NO:32:

( i ) SEQUENCE CHARACTERISTICS:
        ( A ) LENGTH: 381 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:32:

| | | | | | | |
|---|---|---|---|---|---|---|
| TCAAAAAGAA | CATTTCTTCT | GAGTGGTGAG | GGGTCCGTTA | GAGCACACTC | GCTCCTTGGA | 60 |
| AGAGATGTTT | TTTTGATAT | TAGGAACCAA | TAGAATATTT | AGAATTAAT | TTAGATTAAA | 120 |
| TTATAGAAGG | GTATCTGTAG | CGATAAGTTT | CCATTTCAAA | TTTTTCTGAT | GCAGTAGTAT | 180 |
| GTTCTTTTCT | AAAATAAAT | GATAGTTTAT | TAATGATTAA | ACTAATTATT | ATCCTTTGGC | 240 |
| CATCTTTTTC | TACATTTTCC | AGAAACAGAT | CTAATTACGT | TTTTGCTATC | TATAATTATT | 300 |
| AAAAATAATC | ATATATCTTT | AAAGTTGACC | TCAACGTCTT | AAAATGTTTA | GTTTTTAAT | 360 |
| TAACCCTAAA | CCCTAGAACA | C | | | | 381 |

( 2 ) INFORMATION FOR SEQ ID NO:33:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

| | | | | |
|---|---|---|---|---|
| ATTTAGGTGA | CACTATAGAA | GCTATTGGAC | CAGACGGGAA | C | 41 |

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

GACGAGGCAT TTGGCTACC                                                  1 9

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

GGGTGAACAA TCCAACGCTT ACCG                                         2 4

IN VITRO ASSAY FOR INHIBITORS OF THE INTRON SELF-SPLICING REACTION IN *PNEUMOCYSTIS CARINII*

This is a continuation application of patent application Ser. No. 08/068,248 filed on 27 May 1993, now abandoned which application is a continuation-in-part of application 07/922,987, filed 30 Jul. 1992 now abandoned.

BACKGROUND OF THE INVENTION

1. Field of the Invention

This invention relates to a method for assaying for inhibitors of the catalytic Group I self-splicing intron reaction in the nuclear rRNA genes of *Pneumocystis carinii*. More particularly, this invention relates to a method for assaying for self-splicing intron inhibitors which comprises preparing a labeled RNA precursor by transcription of a DNA template containing the intron from the 26S rRNA gene in *Pneumocystis carinii* and a portion of the 5' and 3' flanking exons, incubating the RNA precursor and the inhibitor in the presence of guanosine triphosphate and magnesium ions, and determining the degree of inhibition on the intron splicing reaction by measuring the amount of labeled splicing intermediates and products. This invention may also be modified and used to test the activity of any compound acting on an RNA target to alter its catalytic or template activities in an in vitro assay system.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

*Pneumocystis carinii* (*P. carinii*) is a ubiquitous eukaryotic microorganism causing asymptomatic infections in most humans early in childhood (1) but causing life-threatening pneumonia in immunosuppressed hosts including patients with Acquired Immune Deficiency Syndrome (AIDS, 2). Although morphologically *P. carinii* has properties associated with both protozoa and yeasts, the 16S rRNA coding sequence of *P. carinii* grown in immunosuppressed rats most resembled that of the yeast *Saccharomyces cerevisiae* (*S. cerevisiae*, 3). This sequence also included a 390 base pair insertion resembling a Group I intron, located 31 nucleotides from the 3' end of the rRNA gene (3). Absence of this sequence from mature 16S rRNA (4) and demonstration of its ability to spontaneously excise from transcripts of cloned fragments of the gene (5) confirmed its identity as a self-splicing intron (6–7). The sequence of the 5S rRNA of *P. carinii* grown in nude rats showed closer similarity to 5S rRNA of Amoeba and Myxomycota than to that of Ascomycetes such as Saccharomyces (8). However, the validity of 5S rRNA sequence analysis as a taxonomic tool has been questioned (9). In *S. cerevisiae*, the 5S rRNA is encoded in the same genomic repeated element encoding 16S, 5.8S and 26S rRNAs, but on the opposite strand (reviewed in 10), although most eukaryotes studied do not have the gene for 5S rRNA linked to those for the other rRNA species. Hybridization of chromosomal DNA separated by pulsed field electrophoresis with 16S rRNA-derived probes has localized the 16S rRNA gene of Pneumocystis to one or two 500 kbp. chromosomal DNAs, with the gene for 5S rRNA apparently located elsewhere (11–12).

As set out above, unlike mammalian cells, *P. carinii* has group I self-splicing introns in its rRNA genes (44–46). Splicing can be inhibited by some aminoglycosides, tetracycline, and ethidium bromide. Pentamidine, an anti-Pneumocystis agent the mechanism of action of which was previously unknown (47–52), is a potent inhibitor of intron splicing.

Although pentamidine isethionate and the combination of trimethoprim and sulfamethoxazole have both proven useful for the prophylaxis and treatment of *P. carinii* pneumonitis (PCP), neither treatment is always effective or without serious side-effects (47), signifying the need for new chemotherapeutic agents. Pentamidine has long been used to treat PCP (48). Comparison of the relative activities of a series of aromatic diamidino compounds, including pentamidine, against experimental PCP has shown that the mechanism of action is not inhibition of proteases, thymidylate synthetase (49), dihydrofolate reductase, or DNA polymerase II (50). These compounds bind strongly to DNA, but binding has not been correlated with activity against PCP (51). Recently, inhibition of DNA topoisomerases from *P. carinii* has been suggested as a mechanism of pentamidine action (52).

Sequence analysis and in vitro assays have shown that the nuclear gene encoding 16S rRNA of *P. carinii* contains near its 3' terminus a group I intron capable of catalyzing its own excision from an RNA transcript (44–46). A similar intron sequence in the gene for 26S rRNA of this organism is described herein. Such introns are widespread among various phyla but have not yet been found in the nuclear genomes of the metazoa, including humans (53–54).

The sequence of the coding region of the rRNA operon of rat-derived *P. carinii* has been completed including the genes for 5.8S and 26S rRNA. These genes show homology to the rRNA genes of yeast, and an apparent group I self-splicing intron is present in the 26S rRNA gene (65).

BRIEF DESCRIPTION OF THE FIGURES

FIG. 2 shows the total contiguous sequence determined for *P. carinii* from immunosuppressed Sprague-Dawley rats (Sasco) by the strategy shown in FIG. 1A. Except for the last 18 nucleotides (shown in lower case), capital letters indicate rRNA coding sequences (positive strand), lower case letters indicate spacers, and underlined lower case letters indicate Group I introns. The initial 22 nucleotides are from the 3'-terminal portion of the Group I intron in 16S rRNA. Nucleotides 23–53 are the second exon of 16S rRNA, 54–216 are internal transcribed spacer 1 (ITS1), 217–374 the gene for 5.8S rRNA (identified by similarity to other 5.8S rRNA sequences), 375–556 ITS2, and 557–4256 are the gene for 26S rRNA, with a Group I intron sequence in lower case underlined. This sequence has been deposited at EMBL/GenBank under accession No. M86760 (SEQ ID NO:31).

FIG. 3 shows a comparison of the sequence of the 5.8S rRNA gene of *P. carinii* shown in FIG. 2 with the homologous sequences from *Saccharomyces cerevisiae* (23) shown as Sc, *Tetrahymena pyriformis* (*T. pyriformis*) (24) shown as Tp, and Homo sapiens (25) shown as Hs. Since the actual 5.8S rRNA sequence was not determined, the termini of the *P. carinii* gene have been chosen based on the known sequence of the homologous gene of *S. cerevisiae*, to which it appears to be closely related. The three nucleotides 5' to the proposed rRNA 5' terminus are shown here in lower case letters.

FIG. 5 shows a comparison of the sequence of the 26S rRNA genes of *P. carinii* (Pc) from FIG. 2, with homologous sequences from *S. cerevisiae* (Sc), and *T. pyriformis* (Tp). The Group I self-splicing introns in the *P. carinii* and *T. pyriformis* genes have been omitted. The final 18 nucleotides of the *P. carinii* sequence were determined from organisms from immunosuppressed Hooded rats as shown in FIG. 2.

FIG. 7 shows the sequence of the region from nucleotides 485 through 964 of the 26S rRNA gene from *P. carinii* from Sprague-Dawley rats, as shown in FIG. 5 (Pc1). This sequence was determined for three PCR products made using oligonucleotides 4016 and 2892 as primers and for PCR products made using the oligonucleotide pair 3425 and 3426, and the pair 2893 and 2982, each resulting in products partially overlapping this region. This entire sequence was thus determined on four or five isolates, with four separate sequence determinations made for each PCR product. The sequence of DNA amplified using the same primers (4016 and 2892) from *P. carinii* from Hooded rats is shown as Pc2. The homologous regions of genes from *S. cerevisiae* (Sc) and *T. pyriformis* (Tp) are also shown. The numbering is according to the 26S rRNA sequence of Pc1 as in FIG. 5. The sequence denoted Pc2 has been deposited at EMBL/GenBank under accession No. 86761.

FIG. 8 shows a comparison of the sequences of the region from nucleotides 2911 through 3327 of the 26S rRNA gene of *P. carinii* (Pc1) from Sprague-Dawley rats (FIG. 5) with the homologous regions from *P. carinii* from Hooded rats (Pc2) and from *S. cerevisiae* (Sc) and *T. pyriformis* (Tp). The fragment denoted Pc1 was amplified using primers 4138 and 4170. The sequence shown for Pc2 was determined based on amplifications using primer pair 4138 and 4139 and pair 4169 and 4170, and ligation-dependent PCR amplification of a fragment extending from oligonucleotide 3427 through a PstI site 381 nucleotides past the 3' end of the 26S rRNA gene. The sequences of homologous regions of the 26S rRNA genes of *S. cerevisiae* (Sc) and *T. pyriformis* (Tp) are shown.

FIG. 10 shows the sequence of the spacer region 3' to the 26S rRNA gene of *P. carinii* from Hooded rats (FIG. 10), which was determined by ligation-dependent PCR as described in the text. The sequences for Pc2 shown in FIGS. 8 and 10 have been deposited at EMBL/GenBank under accession No. M86759 (SEQ ID NO:32).

FIGS. 13A through 13D show the inhibition of intron splicing by antibiotics. All experiments were done with 660 nucleotide RNA precursor. In vitro splicing of [$^{32}P$]RNA precursor was performed in the presence of 5 mM $MgCl_2$ and 100 µM GTP (unless otherwise indicated) at 37° C. for 20 minutes as in FIG. 12. Splicing of unpurified transcripts extracted from SP6 RNA polymerase reactions was performed with 12.5 nM of [α-$^{32}P$]GTP replacing non-radioactive GTP. Bands are identified as in FIG. 12. FIG. 13A: Inhibition by gentamicin and tetracycline. Purified [$^{32}P$]RNA precursor splicing was performed as indicated. Lane 1, control without GTP; lane 2, complete reaction without antibiotics; lanes 3–7, gentamicin present at 50, 100, 200, 250 and 500 µM; lanes 8–12, tetracycline present at 10, 50, 100, 200, and 400 µM. FIG. 13B: Inhibition of intron splicing by gentamicin and tetracycline. Splicing of non-radioactive RNA was assayed in the presence of [$^{32}$P]GTP with no antibiotic (lanes 1 and 7), with 50, 100, 200, 300, and 500 μM gentamicin (lanes 2–6), and with 50, 100, 200, and 400 μM tetracycline (lanes 8–11). FIG. 13C: Splicing inhibition by ethidium bromide. Reactions of [$^{32}$P]RNA precursor were run in the presence of 10 μM GTP (except lane 1 which contained neither GTP nor ethidium bromide); lanes 2–7, reactions run in the presence of ethidium bromide at 0, 0.5, 1, 5, 10, and 25 μM, respectively. Similar levels of inhibition were observed in reactions run in the presence of 100–500 μM GTP. FIG. 13D: Inhibition of splicing by ethidium bromide, as measured by incorporation of [α-$^{32}$P] GTP. Lanes 1–5, reactions run in the presence of 0, 0.5, 1, 5 and 25 μM ethidium bromide, respectively.

FIG. 14A: Assays of splicing of [$^{32}$P]RNA precursor. Lane 1, reaction run in the absence of GTP; lanes 2–7 contained 0, 180, 200, 250, 300, and 500 μM pentamidine isethionate, respectively. FIG. 14B: Assays of splicing by [α-$^{32}$P]GTP incorporation. Lane M is as described in FIG. 12. Lanes 1–5 contain products of reactions run in the presence of 0, 160, 180, 200, and 250 μM pentamidine isethionate, respectively.

SUMMARY OF THE INVENTION

Figure 1:
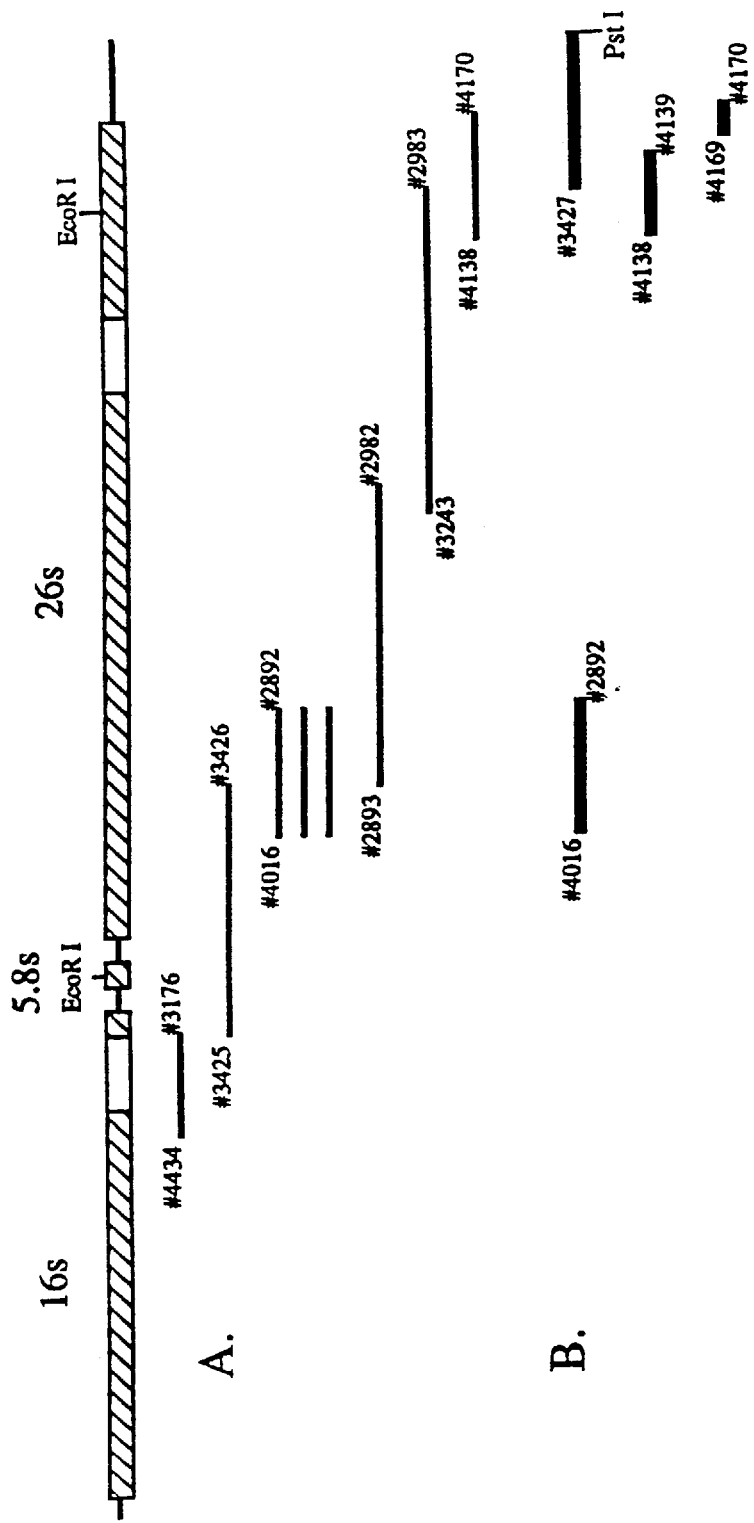
FIG. 1 shows the DNA sequence of a portion of the rRNA-encoding gene(s) of *P. carinii* isolated from immunosuppressed Sprague-Dawley rats (Sasco) and the PCR amplifications which were subsequently cloned and sequenced. The top line represents the DNA sequence of a portion of the rRNA-encoding gene(s) of *P. carinii* isolated from immunosuppressed Sprague-Dawley rats (Sasco). The horizontal lines below represent PCR amplifications which were subsequently cloned and sequenced. Thin lines (1A) refer to PCR products from Sprague-Dawley rats (Sasco) and heavy lines (1B) refer to PCR products from Hooded rats. Numbers refer to oligonucleotide primers (Table 1) used in each PCR reaction.
Figure 4:
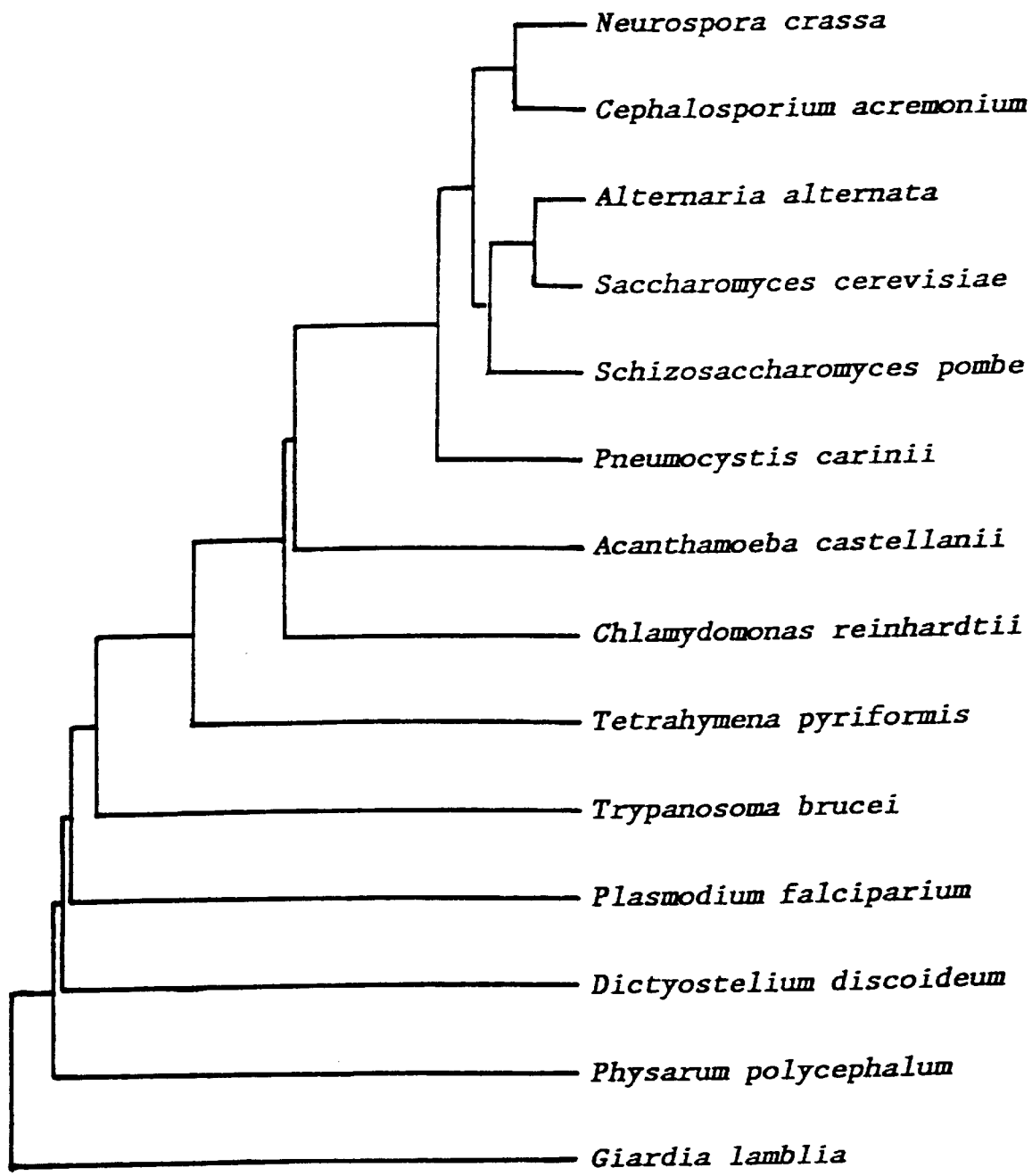
FIG. 4 is a dendrogram generated by the "pileup" program of the Wisconsin- GCG package indicating sequence similarity (but not necessarily evolutionary relationships) among the 5.8S rRNAs compared in Table II.

The present invention pertains to an in vitro method for assaying for an inhibitor of the catalytic Group I self-splicing intron reaction in the nuclear rRNA genes of *Pneumocystis carinii* which comprises the steps of (a) providing a DNA template containing the intron (I) from the 26S rRNA gene in *Pneumocystis carinii* and a portion of the 5' and 3' flanking exons (E1 and E2, respectively) between nucleotides 1963 and 2267 of 26S rRNA (660 nucleotides of amplified rRNA gene including the group I intron); (b) preparing an RNA precursor by transcription of the DNA template in the presence of labeled nucleoside triphosphates to produce a labeled RNA precursor (E1-I-E2); (c) purifying the RNA precursor; (d) incubating the RNA precursor and the inhibitor in the presence of guanosine triphosphate and magnesium ions; and (e) determining the degree of inhibition by the inhibitor on the intron splicing reaction in the RNA precursor by measuring the amount of labeled splicing intermediates and splicing products.

In another embodiment, the present invention pertains to an in vitro method for assaying for an inhibitor of the catalytic Group I self-splicing intron reaction in the nuclear rRNA genes of *Pneumocystis carinii* which comprises the steps of (a) providing a DNA template containing the intron (1) from the 26S rRNA gene in *Pheumocystis carinii* and a portion of the 5' and 3' flanking exons (E1 and E2, respectively) between nucleotides 1963 and 2267 of 26S rRNA (660 nucleotides of amplified rRNA gene including the group I intron); (b) preparing an RNA precursor by transcription of the DNA template to produce a RNA precursor (E1-E2); (c) purifying the RNA precursor; (d) incubating the RNA precursor and the inhibitor in the presence of labeled guanosine triphosphate and magnesium ions; and (e) determining the degree of inhibition by the inhibitor on the intron splicing reaction in the RNA precursor by measuring the amount of labeled splicing intermediates and splicing products.

DETAILED DESCRIPTION OF THE INVENTION

Testing for anti-*Pneumocystis carinii* drugs is conventionally carried out in immunosupressed or genetically immunodeficient animals, making such testing costly and time consuming. Applicants have discovered that the ribosomal RNA genes of *Pneumocystis carinii* contain one or two self-splicing introns which must be removed from the RNA in order for the RNA to function. The self-splicing reaction involves cleavage and religation of the RNA precursor which results in the excision of the intron (I) and attachment of two flanking segments of RNA (E, exons). Applicants have developed an in vitro assay for inhibitors of the self-splicing intron reaction in the nuclear rRNA genes of *Pneumocystis carinii* which allows for the screening of potential anti-*Pneumocystis carinii* drugs before more costly animal testing is conducted.

Applicants's method for assaying for inhibitors of the self-splicing intron reaction in *Pneumocystis carinii* comprises preparing a labeled RNA precursor by transcription of a DNA template containing the intron from the 26S rRNA gene in *Pneumocystis carinii* and a portion of the 5' and 3' flanking exons, incubating the RNA precursor and the inhibitor in the presence of guanosine triphosphate and magnesium ions, and determining the degree of inhibition on the intron splicing reaction by measuring the amount of labeled splicing intermediates and products.

The RNA precursor is prepared by transcription of a suitable DNA template by bacteriophage SP6 DNA-dependent RNA polymerase followed by purification of the RNA precursor by polyacrylamide gel electrophoresis. The DNA templates contain a 17-nucleotide SP6 promoter directly linked to complementary DNA (cDNA). The SP6 promoter/cDNA construct can be in a recombinant DNA plasmid linearized by cleavage with a suitable restriction enzyme or can be prepared by polymerase chain reaction amplification of a precursor-RNA-derived CDNA with two oligodeoxyribonucleotide primers, wherein one primer is collinear with the 5' terminus of the RNA precursor and has a 17-nucleotide extension on its terminus consisting of the positive strand of a consensus bacteriophage SP6 promoter and the other primer is collinear with the reverse complement of the 3' terminus of the RNA precursor. The DNA template can be prepared by amplifying by polymerase chain reaction the intron from the 26S rRNA gene and a portion of the 5' and 3' flanking exons. The portion of the 5' and 3' flanking exons may be between nucleotides 1963 and 2267 of 26S rRNA (660 nucleotides of amplified rRNA gene including the group I intron). For generation of fragments of convenient size in the in vitro splicing reaction, different primers may be used to amplify different portions of the rRNA gene to generate splicing precursors of varying sizes. Preferably, the presursor RNA containing the intron and nucleotides 1963 to 2267 of rRNA (660 nucleotides of amplified rRNA gene including the group I intron) is used. The assay may also be used with exons as short as 67 nucleotides (5' exon) and 26 nucleotides (3' exon).

The resulting RNA transcripts, after purification by polyacrylamide gel electrophoresis, show ribozyme activity catalyzing removal of the intron and ligation of the flanling exon fragments in a reaction requiring guanosine, which can be provided as guanosine triphosphate (GTP), and magnesium. When an inhibitor of the splicing reaction, such as pentamidine, is added to the reaction, the splicing reaction is inhibited.

The extent of the splicing reaction can be measured by (a) using labeled RNA precursor, synthesized in the presence of radioactive nucleoside triphosphates, such as α-$^{32}$P-GTP, and measuring the production of the splicing intermediates and products by autoradiography, after polyacrylamide gel electrophoresis, by quantitatively calculating the radioactivity in each band or, (b) carrying out the self-splicing reaction in the presence of α-$^{32}$P-GTP and using polyacrylamide gel electrophoresis to measure isotope incorporation into the reaction intermediate and linear intron product which contain the covalently linked labeled guanosine moiety added during the self-splicing reaction.

A yeast strain with a *Pneumocystis carinii* derived intron inserted by recombinant DNA methods into an essential gene (URA3) may be employed for an assay for splicing inhibition in living cells. This strain will show growth inhibition in response to splicing inhibitors capable of entering the cell and reaching the sites at which the self-splicing reaction catalyzed by nuclear Group I introns occurs. This cellular system will provide an additional test after the in vitro method demonstrates candidate compounds capable of inhibiting the splicing reaction per se.

The term "oligonucleotide" as used herein refers to primers, probes, oligomer fragments to be detected, oligomer controls, and unlabeled blocking oligomers. Oligonucleotide are molecules comprised of two or more deoxyribonucleotides or ribonucleotides.

The term "primer" as used herein refers to an oligonucleotide, preferably an oligodeoxyribonucleotide, either naturally occurring such as a purified restriction digest or synthetically produced, which is capable of acting as a point of initiation of synthesis when subjected to conditions in which synthesis of a primer extension product, which is complementary to a nucleic acid strand, is induced, i.e., in the presence of nucleotides, an agent for polymerization such as a DNA polymerase, and a suitable temperature and pH. The primer must be sufficiently long to prime the synthesis of extension products in the presence of the polymerization agent.

Diagnostic Probes for Pneumocystis Carinii

In accord with the method of the present invention, the sequence of the portion of the major rRNA-encoding operon (encoding the 16S, 5.8S and 26S rRNA molecules specific for *P. carinii*) from organisms derived from the lungs of immunosuppressed rats, including the genes for 5.8S and 26S rRNAs, has been determined. These two genes show similarity to the homologous genes of *S. cerevisiae*, with the gene for 26S rRNA containing a Group I self-splicing intron.

The relatedness of different Pneumocystis isolates has been difficult to determine in the absence of a long-term culture method for this organism. The 5S rRNA gene amplified by polymerase chain reaction (PCR) from multiple infected humans and rats had the identical sequences (13). However, rat and human-derived organisms showed sequence differences in their mitochondrial DNA (14). When portions of the 26S rRNA gene from two different sources were sequenced, phylogenetically variable regions of the gene were found to be different between these two organisms. This marked sequence difference between 26S rRNA gene sequences may represent differences between clones of the same species or may indicate the existence of more than one species within the genus Pneumocystis. In either case, such differences may provide a mechanism of recognizing the relationships between different individual Pneumocystis isolates for epidemiological studies. This appears to be the first such difference reported between Pneumocystis isolates in the sequence of a chromosomal gene.

The rRNA Operon of *Pneumocystis carinii*

Although the exact phylogenetic relationship of *P. carinii* to other species remains unknown, the 5.8S and 26S rRNA genes, like that for 16S rRNA (3), are similar in primary sequence to the homologous genes of *S. cerevisiae*. This finding contrasts with the report that the 5S rRNA gene most resembles the sequence of the homologous genes of Amoeba or Myxomycota rather than those of the Ascomycetes (8). The organization of the major rRNA operon of *P. carinii* differs from that of *S. cerevisiae* in that for the former there is no evidence that the 5S rRNA and 16S-5.8S-26S rRNA operon genes are part of the same repeated DNA unit, based on pulsed field electrophoresis studies (11–12). Linkage of the 5S rRNA gene to genes encoding 16S rRNA or 26S rRNA by PCR techniques has not been observed. The amount of DNA obtained from *P. carinii* was limited, and so classical Southern analysis was not attempted.

The presence of Group I self-splicing introns in the 16S and 26S rRNA genes of *P. carinii* distinguishes this organism from *S. cerevisiae* and from its mammalian hosts. Since various compounds can specifically inhibit the splicing of Group I introns in vitro (31), Group I intron splicing may provide a specific target for development of new therapeutic agents against *P. carinii.*

Taxonomy of *Pneumocystis carinii*

The exact taxonomic relationships of *P. carinii* remain uncertain, in part due to the limited number of eukaryotic microorganisms whose rRNA sequences are known. Furthermore, the definitions of the groups denoted as Fungi and Protozoa are so broad and imprecise that each includes very distantly related organisms. It is possible that once more organisms of this type are studied, these two groupings may prove to be inadequate, and the taxonomy of the eukaryotic microorganisms may require some redefinition. This has already proven to be the case for the Microsporidia, which have been placed in a group distinct from all other eukaryotic microorganisms on the basis of their rRNA sequences (32).

In the absence of a long-term culture method or other tools for comparison of different *P. carinii* organisms, the number of species within the genus Pneumocystis is undefined. Antigenic differences between *P. carinii* obtained from different mammalian host species have been demonstrated (33–36), although their genetic basis is not proven. Although the 5S rRNA gene sequences of multiple human and rat isolates of *P. carinii* are identical (13), such isolates differ in the sequence of their mitochondrial DNA (14). DNA hybridization methods with a cloned DNA fragment have also suggested the non-identity of human and rat-derived *P. cainii*, with differences noted among different human, but not rat, isolates (37). Based on these results, it has been suggested that subspecies of *P. carinii* may be designated based on the hosts from which they are isolated (38).

The data presented herein show that multiple differences exist between the 26S rRNA gene sequences of *P. carinii* from Sprague-Dawley rats from Sasco which were immunosuppressed in isolation (and therefore presumably infected at some other location prior to their arrival here) and Hooded rats which were immunosuppressed here without isolation (and therefore presumably infected in this building or at some geographic location distinct from the site at which the Sprague-Dawley rats were infected). Since multiple independent PCR amplifications of portions of the 26S rRNA gene prepared from templates derived from different individual rats of the same type yielded identical sequences, there is no evidence that the differences observed between the two sources represent PCR artefacts, sequencing errors, or heterogeneity of rRNA sequences within an individual cell, as has been reported in Plasmodium species (39). This variation between different P. carinii isolates resembles that seen between different individual humans, which also occurs in regions of the 26S rRNA gene which are phylogenetically non-conserved (40). Sequence differences in rRNA genes have been suggested as defining species differences within the genus Giardia (41).

Figure 9:
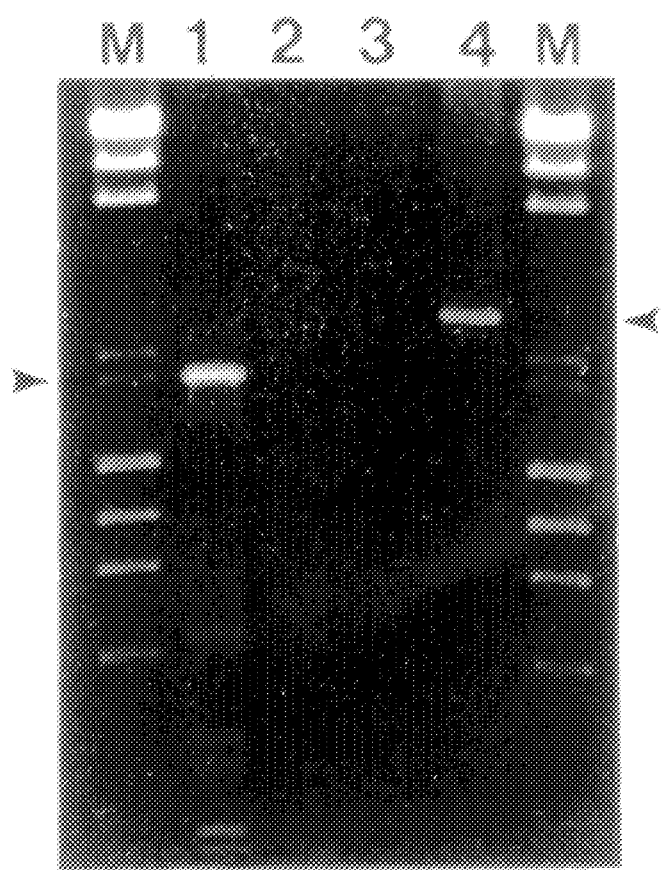
FIG. 9 shows the results of PCR amplification confirming the sequence differences between Pc1 and Pc2 shown in FIGS. 7 and 8. Primers 4358 and 4746 were used to amplify Pc1 (lane 1) or Pc2 (lane2) DNA templates. Primers 4743 and 4744 were used to amplify Pc1 (lane 3) or Pc2 (lane 4) DNA. Lanes M contain a mixture of HindIII digested bacteriophage lambda DNA and HaeIII digested replicative form DNA of bacteriophage/X174 (BRL).

When Pc1 DNA template was amplified by PCR using the primer pair 4358 (universal) and 4746 (Pc1-specific), the expected 2,067 bp product was produced; in contrast, no product was generated from Pc2 template with these same primers (FIG. 9). Similarly, primers 4743 (Pc2-specific) and 4744 (Pc2-specific) amplified an approximately 3.0 kbp product from Pc2 template; no similar product was seen with Pc1 template (FIG. 9). Note that in some reactions a barely detectable band of the same size seen with Pc2 template was seen with Pc1 template using the latter primer pair. These data are consistent with Pc1 and Pc2 each containing predominantly genes encoding single distinct major 26S rRNA sequences.

Comparisons of the sequences of multiple P. carinii rRNA gene regions should determine the extent of variability present. If different human isolates of this organism vary as much as do different rat isolates, then these sequences could be useful as epidemiological markers for identifying strains of P. carinii and studying the spread of the organism and the relative roles of new infection versus reactivation of earlier asymptomatic colonization in the development of P. carinii pneumonitis in immunosuppressed humans, including patients with AIDS. Since different species of Tetrahymena differ more in their intron sequences than in the sequences of adjacent conserved regions encoding rRNA (27), such regions may prove to be even more variable between different P. carinii organisms. Further studies may determine the variability within and between species of the internal transcribed spacers (between the 16S and 5.8S rRNA and 5.8S and 26S rRNA genes) and external transcribed spacers (flanking the rRNA coding regions). If these spacers contain regions with specific functions in rRNA transcription or processing (30), such regions may show sequence conservation. Preliminary data show a lack of specific conservation between the internal transcribed regions of isolates Pc1 and Pc2.

In vitro Assay for Drugs Inhibiting Intron Splicing in *Pneumocystis carinii*

As set out above, group I intron splicing represents a specific target for chemotherapy for PCP. This approach has previously been suggested for development of antifungal agents, based upon the presence of group I introns in the mitochondria of many fungi (55).

Group I introns contain a guanosine binding site and catalyze a reaction in which guanosine (or a guanosine nucleotide) attacks the 5' residue of the intron to produce the 5' exon (E1) and guanosine-intron-3' exon (I-E2) intermediates, which then further react to yield linear guanosine-intron (I) and the spliced 5' exon-3' exon product (E1-E2). Excision of the intron in vitro can be assayed by the conversion of radioactive RNA containing the intron to the various intermediates and products of the reaction, or by the incorporation of radioactivity from $[\alpha\text{-}^{32}P]GTP$ into the I-E2 intermediate and I product. Amplification of the splicing precursor containing the intron from the 26S rRNA gene of P. carinii and assays of splicing were performed as described in FIG. 11.

Figure 12:
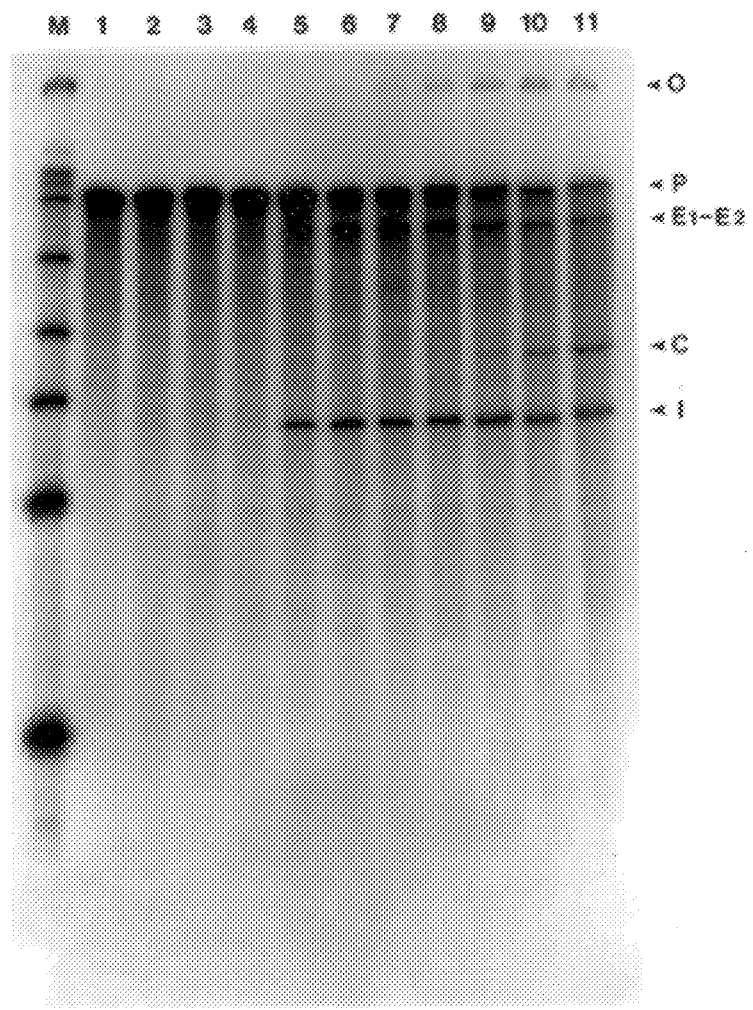
FIG. 12 shows the requirement for $Mg^{++}$ for in vitro splicing. Radioactive RNA precursor (1296 nucleotides, 1 nM) was incubated at 37° C. for 30 minutes in the presence of 50 mM Tris-HCl, pH 7.5, 0.4 mM spermidine, 4 units of RNasin, 100 µM guanosine triphosphate (GTP) and the indicated concentrations of $MgCl_2$ in a volume of 10 µl. Reactions were terminated by addition of 10 µl of 8M urea containing 5 mM Na-EDTA, pH 8.0, and 0.025% each of bromphenol blue and xylene cyanol, followed by heating at 65° C. for 3 minutes and PAGE, with visualization by autoradiography. Lane M contains RNA standards (molecular weights 1.77, 1.52, 1.28, 0.78, 0.53, 0.40, 0.28, and 0.16 kd, BRL), 5'-labeled with $^{32}p$ using bacteriophage T4 polynucleotide kinase (Pharmacia). Lane 1, purified RNA precursor; lane 2, GTP omitted, 5 mM $MgCl_2$; lane 3, no $MgCl_2$, 1 mM EDTA; lanes 4–11, reactions run in the presence of 0, 1, 5, 25, 50, 100, 200 or 500 mM $MgCl_2$, respectively. O indicates origin; P, RNA precursor; I, linear intron; E1-E2, spliced RNA product; C, presumed circularized intron. Bands corresponding to the 5' exon (E1) and G-intron-3' exon (I-E2) are not visible on this exposure.

As shown in FIG. 12, splicing requires $Mg^{++}$, with concentrations from 1 to 500 mM allowing the reaction to proceed. At very high concentrations of $MgCl_2$ an additional band is produced from radioactive RNA precursor, which has been confirmed by sequence analysis to be a circularized form of the intron, previously observed as a product of further reaction of other excised linear group I introns (58–60). Isolated linear intron reacts to produce this circular form in the presence of 100 mM $MgCl_2$. The splicing reaction was unaffected by pH in the range 6.4 to 8.5, and $(NH_4)_2SO_4$ up to 50 mM had no effect, although splicing was severely inhibited by concentrations above 200 mM. The reaction required GTP, which was replaceable by equal concentrations of guanosine monophosphate (GMP), or guanosine diphosphate (GDP), but not by adenosine triphosphate (ATP), cytidine triphosphate (CTP) or uridine triphosphate (UTP). The bands in FIG. 12 are consistent with the predicted sizes of the indicated intermediates and products of the splicing reaction. When RNA precursor was prepared from PCR products made using different primers, the sizes of the exon fragments were altered and the mobilities of exon-containing bands were appropriately shifted, while the mobility of linear and presumed circular intron remained unchanged.

Figure 13A:
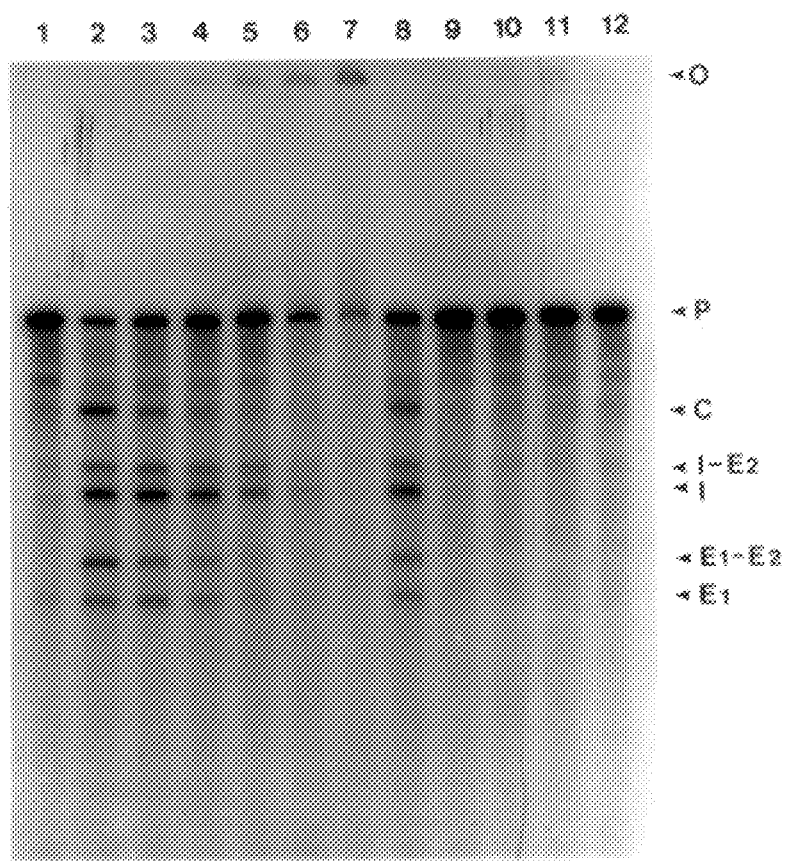

As demonstrated in FIG. 13A, the aminoglycoside gentamicin inhibited splicing of the 26S rRNA intron of P. carinii. Similar inhibition was caused by kanamycin A and streptomycin, but required higher concentrations of those antibiotics. Inhibition by aminoglycosides of splicing of other group I introns has previously been described (55,61). These antibiotics also inhibited splicing of the intron from the 16S rRNA gene of P. carinii. Some radioactivity remaining at the gel origin and a decrease in precursor entering the gel in the presence of high levels of gentamicin (FIG. 13A) may reflect RNA binding by the antibiotic. When splicing was assayed by incorporation of $[\alpha\text{-}^{32}P]GTP$ into I and I-E2(FIG. 13B), the reaction was less sensitive to gentamicin than was splicing of radioactive RNA precursor (FIG. 13A). A very broad band of radioactivity, apparently due to binding of GTP to the antibiotic, was observed in the lower portion of gels run on splicing reactions assayed with $[\alpha\text{-}^{32}P]GTP$. A similar band was observed in reactions run in the absence of RNA. It has been suggested (61) that inhibition of splicing by aminoglycosides is due to antibiotic competition for the G-binding site of the intron. This mechanism would be consistent with the lack of inhibition of splicing of group II introns by these agents (55,61). As previously reported for other group I introns (55), the aminoglycoside, G418, failed to inhibit splicing at 500 μM. Kinetic analysis has confirmed that streptomycin inhibits intron splicing by competition with guanosine.

The amino acid arginine has been noted to inhibit splicing by the group I intron in the Tetrahymena 26S rRNA gene. Mutants in the conserved P7 helix which functions in G binding render this ribozyme resistant to arginine (62). The intron in the 26S rRNA gene of Pc1 is similarly inhibited competitively by high concentrations of arginine and shares structured features with the Tetrahymena intron (62) which shows similar argine sensitivity. The inhibitory activity of arginine is greater for L-arginine than D-arginine and citrulline shows no detectable inhibition. On the other hand, polymers of L-arginine are much more potent than arginine, with tri-arginine being at least 1,000 times more potent than L-arginine. L-arginine and its polymers act by inhibiting the first step of the splicing reaction; kinetic analysis shows that L-arginine and its polymers activate the second step of the reaction. When arginine analogues and polymers were tested, the order of potency in inhibiting the first step and stimulating the second step of the splicing reaction was virtually identical suggesting that both effects may be due to interaction of these compounds with the same site on the ribozyme.

Figure 13B:
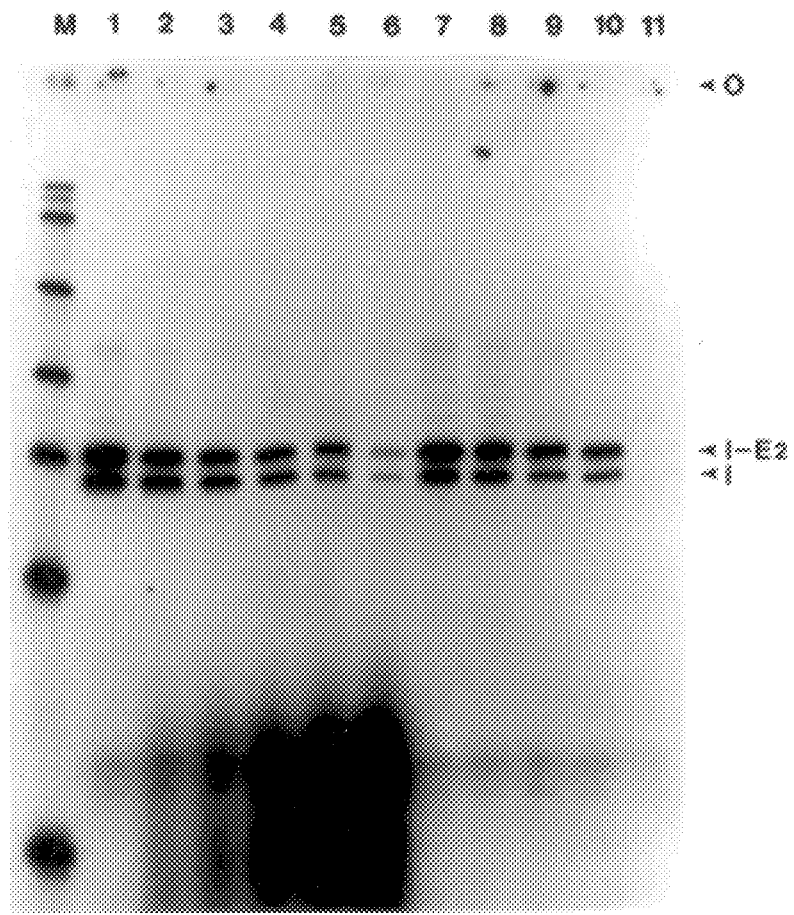

In addition to the aminoglycosides, the protein synthesis inhibitor tetracycline also inhibits RNA splicing (FIGS. 13A and 13B). Kinetic analysis reveals that this inhibition is non-competitive with GTP unlike inhibition by streptomycin or arginine. Addition of tetracycline did not result in significant binding of RNA to the origin or gel shift of GTP. Since the chemical structure of tetracycline and the mechanism of translational inhibition by this antibiotic differ from those of the aminoglycosides, its mechanism of splicing inhibition may also be distinct. This mechanism may relate to its planar aromatic ring structure which might intercalate into RNA helices. The possible inhibitory effect of helix-distorting intercalators is supported by the potency of ethidium bromide as an inhibitor of intron splicing (FIGS. 13C and 13D), with similar concentrations completely inhibiting splicing by either assay. As reported for other introns (55), other translation inhibitors failed to inhibit splicing by either assay, including chloramphenicol, cycloheximide, puromycin, aurintricarboxylic acid and clindamycin (all from Sigma), at 500 $\mu$M. Ampicillin (Sigma) also failed to inhibit at 500 $\mu$M.

Pentamidine (Sigma) inhibited splicing of the intron from the gene encoding 26S rRNA (FIGS. 14A and 14B) or 16S rRNA of *P. carinii* by both assays. Kinetic analysis revealed this inhibition to be non-competitive and acting on the first step of the splicing reaction. Possibly the two diamidino moieties of pentamidine interact with the G binding site of the intron as has been suggested for the paired or single guanidino groups on some inhibitory aminoglycosides (61). Alternatively, the paired aromatic rings and/or positively charged moieties of pentamidine might act to distort the intron's secondary structure, which is critical to its catalytic function (63). The mechanism of action of pentamidine was previously undefined (49–52), so there was no rational basis for designing more active analogues for future clinical trials. If the ability of pentamidine analogues (49) to inhibit splicing correlates with in vivo activity against experimental PCP then this assay would be useful for this purpose.

The lack of reported group I introns in the nuclear genomes of metazoa (53) makes the intron splicing process an attractive therapeutic target. In the yeast *Saccharomyces cerevisiae*, group I introns have been found only in the mitochondrial genome, and their proper excision is essential for mitochondrial biogenesis and function (53). The growth of this organism has been found to be more sensitive to pentamidine when grown in glycerol than in various fermentable sugars, suggesting a mitochondrial target for pentamidine action in this organism (64). This conclusion is supported by the reduced growth rate of pentamidine resistant mutants on glycerol (64), which would be consistent with altered mitochondrial function.

Clinical utility of candidate agents for anti-PCP chemotherapy will depend on their tissue distribution and cell entry. Tetracycline and aminoglycosides may fail as drugs against PCP because of their inability to enter the pathogen. However, the presence of nuclear group I introns in *P. carinii* suggests splicing of these introns as a target for chemotherapeutic agents. The clinically useful drug pentamidine has anti-splicing activity, as do tetracycline, ethidium bromide, and some aminoglycosides. In vitro splicing represents a rapid screening method to identify chemicals for further testing for treating PCP.

The present invention is further illustrated by the following examples which are not intended to limit the effective scope of the claims. All parts and percentages in the examples and throughout the specification and claims are by weight of the final composition unless otherwise specified.

EXAMPLES

Diagnostic Probes for *Pneumocystis Carinii*
Growth and Purification of *Pneumocystis carinii*

Sprague-Dawley rats from Sasco, Inc. (Omaha, Nebr.) were maintained in isolation cages with protective filters (Lab Products, Maplewood, N.J.) with immunosuppression by addition of dexamethasone (1 mg/ml) and tetracycline (0.5 mg/ml) to their drinking water. Water and autoclaved 8% protein diet (ICN) were provided ad libitum. Hooded rats (Harlan-Sprague-Dawley, Indianapolis, Ind.), were treated in the same way but not isolated. Rats were sacrificed after 8–12 weeks of immunosuppression or when signs of respiratory distress were observed. All subsequent procedures were done at 4° C. Each pair of lungs was removed, minced with a scissors and the homogenate was suspended in 25ml of Dulbecco's Modified Eagle's Medium (DMEM) and centrifuged for 10 minutes at 200×g to remove tissue debris and lung cells. The supernatant was then transferred to a fresh tube, cells were collected at 1,600×g and resuspended in 3ml of phosphate buffered saline (PBS). Suspended cells were loaded on discontinuous Percoll gradients (10–40% in 10% steps) and after centrifugation at 1,600×g for 30 minutes, trophozoites were found at the 10–20% interface, cysts with some trophozoites and a few mammalian cells at the 20–30% interface, and predominantly mammalian cells with some cysts at the 30–40% interface.

For in vitro cultivation of *P. carinii*, mink lung cells of line ATCC CCL64 (15) grown to 80% confluence in 10 cm petri dishes in DMEM supplemented with 10% fetal calf serum were used as feeder cells. Percoll gradient purified cysts (5×10$^5$) were added to each plate in the presence of penicillin, streptomycin, gentamicin and fungizone, followed by incubation at 37° C. in a humidified 5% $CO_2$ incubator. After 1–3 days in culture, the plates were gently agitated and the Pneumocystis-containing medium was collected and centrifuged at 100×g for 5 minutes to pellet contaminating detached mammalian cells. Only a few mammalian cells detached during the culture period and these were efficiently removed by the centrifugation.

Microscopic Techniques

Pneumocystis trophozoites were quantitated in 5ul samples air dried on microscope slides and stained with Diff-Quik (Baxter Healthcare Co., Miami, Fla.). Cysts were identified by toluidine blue O stain (16). All quantitation was done by counting three 5ul samples for a total of 30 oil immersion fields for each sample. All cultures and purified Pneumocystis preparations were negative for fungal and bacterial contamination by microscopy and culture, and for Mycoplasma contamination by MycoTect kit (Gibco BRL).

Extraction of Nucleic Acids from Trophozoites

*P. carinii* cells from mink lung cell cultures were harvested by centrifugation at 3,000 rpm for 30 minutes at 4° C. in a Sorvall SS-34 rotor, and were washed with chilled PBS. Cells were resuspended in 50 mM Tris-HCl [Tris (hydroxymethyl)aminomethane hydrochloride], 50 mM Na-EDTA (sodium ethylenediaminetetraacetic acid), pH 8.0, and were lysed by incubation at 65° C. for 30 minutes in the presence of 1% SDS (sodium dodecyl sulfate). Proteins were removed by precipitation on ice in the presence of 1.25M potassium acetate followed by centrifugation at room temperature. Total nucleic acids were then concentrated by precipitation in an equal volume of absolute ethanol on ice.
Oligonucleotides DNA oligonucleotides were synthesized by β-cyanoethyl phosphoramidite chemistry on automated DNA synthesizers (Cyclone, Milligen and 380B, Applied Biosystems), and were purified by chromatography on NENsorb-Prep cartridges (NEN-DuPont) prior to use. Oligonucleotides used are listed in Table 1.

*carinii*. The underlined C in 4169 was present in the 26S rRNA gene of *P. carinii* from Hooded rats but was A in the homologous location in organisms from Sprague-Dawley rats, as described in the text. The underlined C in 3425 is from the published intron sequence (5) but was T in a clone of the intron amplified using flanking exon-derived primers 4434 and 3176. A subsequent Genbank sequence of the authors of the previous report (5) is corrected to agree with these sequences.

Table II shows the extent of genetic identity as indicated by the Wisconsin-GCG "Distances" program. Sequences are from GenBank with the following accession numbers: *Neurosopora crassa*, Nc X02447; *Cephalosporium acremoniun*, Ca X06574; *Alternaria alternata*, Aa X17454; *Saccharomyces cerevisiae*, Sc K01051; *Schizosaccharomyces pombe*, Sp J01359; *Pneumocystis carinii*, Pc; *Acanthamoeba castellani*, Ac K00471; *Chlamydomonas reinhardtii*, Cr M35013; *Tetrahymena pyriformis*, Tp M10752; *Trypanosoma brucei*, Tb X05682; *Plasmodium falciparum*, Pf J04683; *Dictyostelium discoideum*, Dd V00192; *Phyarum polycephalum*, Pp M13612; and *Giardia lamblia*, Gl M35013.

TABLE 1

Oligonucleotides Used for PCR Amplifications and Sequencing

| No. | Sequence | 5' Coordinate | Ref. |
|---|---|---|---|
| 228A | AACAGCTATGACCATGAT | pUC polylinker | SEQ ID NO:1 |
| 229 | TTCCCAGTCACGACGTTG | pUC polylinker | SEQ ID NO:2 |
| 230 | TGTAAAACGACGGCCAGT | pUC polylinker | SEQ ID NO:3 |
| 1138 | AGGGATTGGTTGGCCTGGTCCTCCGAA | 637(+), 16S | 3 SEQ ID NO:4 |
| 1887 | CTTTCCAGTAATAGGCTTATCG | 1726(−), 16S | 3 SEQ ID NO:5 |
| 2892 | GCTATCCTGAGGGAAACTTCGG | 964(−), 26S | SEQ ID NO:6 |
| 2893 | CCCGTCTTGAAACACGGACCAAGG | 635(+), 26S | SEQ ID NO:7 |
| 2894 | CCCGCGATCAGCAAAAGCTAATCTGG | 1374(−), 16S | 3 SEQ ID NO:8 |
| 2917 | CCATACAGAAGACCATTCTTTATCCC | 507(−), DHFR | 18 SEQ ID NO:9 |
| 2918 | GGCCGATCAAACTCTCTTCC | 58(+), DHFR | 18 SEQ ID NO:10 |
| 2919 | GGGAAAAGGTCGTGGGGAGCG | 977(−), TS | 17 SEQ ID NO:11 |
| 2920 | GGGGAAGACCGCCCTGATAGG | 58(+), TS | 17 SEQ ID NO:12 |
| 2982 | GAGCCAATCCTTATCCCGAAGTTACG | 1933(−), 26S | SEQ ID NO:13 |
| 2983 | GTCTAAACCCAGCTCACGTTCCC | 2933(−), 26S | SEQ ID NO:14 |
| 3175 | GGGTGGTGGTGCATGGCCG | 1262(+), 16S | 3 SEQ ID NO:15 |
| 3176 | CCTTCCGCAGGTTCACCTACGG | 1796(−), 16S | 3 SEQ ID NO:16 |
| 3243 | CCGCAGCAGGTCTCCAAG | 1833(+), 26S | SEQ ID NO:17 |
| 3425 | CGAAAGAGAGGAGGTAGCACC | 368(+), intron, 16S | 5 SEQ ID NO:18 |
| 3426 | GGTCCGTGTTTCAAGACGGG | 654(−), 26S | SEQ ID NO:19 |
| 3427 | GGGAACGTGAGCTGGGTTTAG | 2911(+), 26S | SEQ ID NO:20 |
| 4016 | GGTTTGGCAGGCCAACATCGG | 485(+), 26S | SEQ ID NO:21 |
| 4138 | CCATGAAAGTGTGGCCTATCG | 2715(+), 26S | SEQ ID NO:22 |
| 4139 | GCCTGGTCAGACAACCGC | 3049(−), 26S | SEQ ID NO:23 |
| 4169 | GGATTATGGCTGAACGCC | 3074(+), 26S | SEQ ID NO:24 |
| 4170 | GGCTTAATCTCAGCAGATCG | 3328(−), 26S | SEQ ID NO:25 |
| 4358 | GACGAGGCATTTGGCTACC | 2267(−), 26S | SEQ ID NO:26 |
| 4443 | GTACACACCGCCCGTCGC | 1631(+), 16S | 3 SEQ ID NO:27 |
| 4743 | TTTAGCTCTTGATTGTAG | 556(+), 26S, Pc2 | SEQ ID NO:28 |
| 4744 | CGCATATTTTATATTATG | 3234(−), 26S, Pc2 | SEQ ID NO:29 |
| 4746 | GTTAGCTCTTGGCTTCTG | 556(+), 26S, Pc1 | SEQ ID NO:30 |

TS refers to the thymidylate synthase (17) and DHFR refers to the dihydrofolate reductase (18) genes of *P. carinii*.

Table 1 lists all primers used for PCR amplifications and sequencing. The underlined G in 3243 was predicted for the 26S rRNA gene sequence based on sequences from other organisms, but was A in the actual 26S rRNA sequence of *P.*

TABLE II

Sequence Similarity of 5.8S rRNAs of Simple Eukaryotes

|    | Nc | Ca | Aa | Sc | Sp | Pc | Ac | Cr | Tp | Tb | Pf | Dd | Pp | Gl |
|---|---|---|---|---|---|---|---|---|---|---|---|---|---|---|
| Nc | 1.0000 | .9299 | .9236 | .9172 | .8599 | .8854 | .7771 | .7308 | .6883 | .6624 | .5159 | .5414 | .5097 | .4483 |
| Ca |  | 1.0000 | .8924 | .8797 | .8544 | .8418 | .7215 | .7244 | .6688 | .6519 | .4873 | .5506 | .4968 | .4828 |
| Aa |  |  | 1.0000 | .9494 | .8987 | .8671 | .7722 | .7436 | .6883 | .6582 | .5380 | .5506 | .5161 | .4483 |
| Sc |  |  |  | 1.0000 | .9114 | .8734 | .7848 | .7564 | .7143 | .6392 | .5316 | .5696 | .5161 | .4483 |
| Sp |  |  |  |  | 1.0000 | .8165 | .7407 | .7500 | .7143 | .5879 | .5273 | .5432 | .5290 | .4759 |

TABLE II-continued

Sequence Similarity of 5.8S rRNAs of Simple Eukaryotes

|    | Nc | Ca | Aa | Sc | Sp | Pc | Ac | Cr | Tp | Tb | Pf | Dd | Pp | Gl |
|----|----|----|----|----|----|----|----|----|----|----|----|----|----|----|
| Pc |    |    |    |    |    | 1.0000 | .7468 | .7051 | .6753 | .6519 | .5063 | .5443 | .5032 | .4207 |
| Ac |    |    |    |    |    |    | 1.000 | .7500 | .6818 | .5679 | .5185 | .5000 | .5032 | .4828 |
| Cr |    |    |    |    |    |    |    | 1.0000 | .6429 | .5641 | .5513 | .4744 | .4516 | .4552 |
| Tp |    |    |    |    |    |    |    |    | 1.0000 | .5844 | .5714 | .5130 | .5000 | .4414 |
| Tb |    |    |    |    |    |    |    |    |    | 1.0000 | .4702 | .4691 | .5161 | .4138 |
| Pf |    |    |    |    |    |    |    |    |    |    | 1.0000 | .4753 | .4452 | .3793 |
| Dd |    |    |    |    |    |    |    |    |    |    |    | 1.0000 | .4065 | .3862 |
| Pp |    |    |    |    |    |    |    |    |    |    |    |    | 1.0000 | .4483 |
| Gl |    |    |    |    |    |    |    |    |    |    |    |    |    | 1.0000 |

TABLE III

Sequence Similarity of 26S rRNAs of Simple Eukaryotes

|    | Pc | Sc    | Tp    | Pp    |
|----|----|-------|-------|-------|
| Pc | —  | 0.833 | 0.739 | 0.623 |
| Sc |    | —     | 0.734 | 0.602 |
| Tp |    |       | —     | 0.605 |

Table III shows the extent of genetic identity of 26S rRNA gene sequences, calculated as in Table II. Abbreviations are as in Table II; sequences from GenBank include Sc, J01355; Tp, X54004; and Pp, V01159.

Amplification and Cloning of DNA

*Pneumocystis carinii* DNA was amplified by means of PCR performed in a DNA Thermal Cycler (Perkin Elmer Cetus) using thermostable DNA polymerase from *Thermus aquaticus* (AmpliTaq, Perkin Elmer Cetus). Reactions were run in the presence of 0.2 mM of each dNTP, 0.4 uM of each of the indicated primers, 10 mM Tris-HCl (pH 8.3), 50 mM potassium chloride, 1.5 mM $MgCl_2$, gelatin (0.001% w/v), and 5 units of AmpliTaq DNA polymerase in 100 ul total volume. Amplifications of over 1 kb. segments were performed by incubation at 95° C. for 2 minutes followed by 30 cycles of 94° C. for 1 minute, 50° C. for 1 minute, and 72° C. for 1.5 minutes, followed by a 7 minute incubation at 72° C. Amplifications of fragments of less than 1 kb. were performed by 2 cycles of 94° C. for 2 minutes, 58° C. for 1 minute, and 72° C. for 45 seconds, followed by 30 cycles of 94° C. for 1 minute, 58° C. for 1 minute, and 72° C. for 1 minute, followed by incubation at 72° C. for 1 minute. For some PCR reactions, the thermostable DNA polymerase from *Thermus thermophilus* (Hot Tub, Amersham) was used, under reaction conditions recommended by the manufacturer using 1.5 units of polymerase in a 100 ul reaction, using 2 cycles of 94° C. for 2 minutes, 58° C. for 1 minute, and 70° C. for 2 minutes, followed by 30 cycles of 94° C. for 1 minute, 59° C. for 1 minute, and 70° C. for 3 minutes, followed by incubation at 70° C. for 10 minutes. After PCR reaction, products were purified by agarose gel electrophoresis, treated with T4 DNA polymerase (BRL) to generate blunt ends, phosphorylated with T4 polynucleotide kinase (Pharmacia), ligated under blunt end ligation conditions to SmaI-cut pUC18 DNA, and transformed into *E. coli* DH5-α competent cells (BRL, Bethesda, Md.) as described (19). Cells were grown in LB medium and plasmid DNA was extracted and purified as described (19).

DNA Sequence Determination

DNA sequence determination was performed on the Genesis 2,000 Automated DNA Sequencer (DuPont) according to the manufacturer's instructions for sequencing reactions run on covalently closed superhelical DNA templates, using DNA polymerase from bacteriophage T7 (Sequenase version 1.0, U.S. Biochemicals). Primers used included oligonucleotides 228A, 229, and 230 (Table 1), which base pair with regions flanking the pUC18 polylinker, and others listed in Table 1. For inserts of over 300 nucleotides without convenient internal primer binding sites, nested deletions were generated as described (19), which were then sequenced using the standard primers. All sequences reported were determined at least twice for each DNA strand.

Results

Sequence of the rRNA Operon of *Pneumocystis carinii*

Prior to use for these experiments, nucleic acids from *P. carinii* were shown to be from that source by confirmation of previously published sequences using PCR methods. Primers 2920 and 2919 used in a PCR reaction yielded a single 920 bp. product (based on agarose gel electrophoresis), the size predicted for the thymidylate synthase gene with its 4 intervening sequences (17). A PCR utilizing primers 2918 and 2917 amplified a single 493 bp. product, as predicted for the dihydrofolate reductase gene with a 43 bp. intervening sequence (18). The *P. carinii*-specific primers for 16S rRNA, 1138 and 2894, yielded a single PCR product of the predicted 738 bp. size (3). The "universal" 16S rRNA primers, 3175 and 3176, generated two PCR products: one was 925 bp. in length, the size predicted for the 16S rRNA gene with its Group I intron (3, 5), and the other was 535 bp. in length. This smaller fragment had a sequence identical to the corresponding region of human 18S rRNA (21), and presumably represents amplification of contaminating mink lung cell ribosomal DNA. The sequence of mink 16S rRNA is unknown, but is presumably closely related to the human sequence.

FIG. 1 shows the DNA sequence of a portion of the rRNA-encoding gene(s) of *P. carinii* isolated from immunosuppressed Sprague-Dawley rats (Sasco) and the PCR amplifications which were subsequently cloned and sequenced. The top line represents the DNA sequence of a portion of the rRNA-encoding gene(s) of *P. carinii* isolated from immunosuppressed Sprague-Dawley rats (Sasco). The horizontal lines below represent PCR amplifications which were subsequently cloned and sequenced. Thin lines (FIG. 1A) refer to PCR products from Sprague-Dawley rats (Sasco) and heavy lines (FIG. 1B) refer to PCR products from Hooded rats. Numbers refer to oligonucleotide primers (Table 1) used in each PCR reaction. Each PCR product, produced using primers listed in Table 1, was cloned into pUC18 and both strands were sequenced at least twice. All overlapping segments yielded the same sequence, indicating an error rate of Taq polymerase-catalyzed PCR (22) of less than one per 500 nucleotides. Rare misincorporation events in the regions which were only amplified once cannot be ruled out.

FIG. 2 shows the total contiguous sequence determined for *P. carinii* from immunosuppressed Sprague-Dawley rats (Sasco) by the strategy shown in FIG. 1A. Except for the last 18 nucleotides (shown in lower case), capital letters indicate rRNA coding sequences (positive strand), lower case letters indicate spacers, and underlined lower case letters indicate Group I introns. The initial 22 nucleotides are from the 3'-terminal portion of the Group I intron in 16S rRNA. Nucleotides 23–53 are the second exon of 16S rRNA, 54–216 are internal transcribed spacer 1 (ITS1), 217–374 the gene for 5.8S rRNA (identified by similarity to other 5.8S rRNA sequences), 375–556 ITS2, and 557–4256 are the gene for 26S rRNA, with a Group I intron sequence in lower case underlined. This sequence has been deposited at EMBL/GenBank under accession No. M86760. The sequence of the final exon of the 16S rRNA gene agrees with that previously reported (3), although the third base from the 3' end of the intron (C) previously reported (5) is absent in our sequence. This sequence has been confirmed in an additional amplified fragment including the entire intron sequence. A subsequent Genbank sequence of the authors of the previous report (5) is corrected to agree with these sequences SEQ ID NO:31.

FIG. 3 shows a comparison of the sequence of the 5.8S rRNA gene of *P. carinii* shown in FIG. 2 with the homologous sequences from *Saccharomyces cerevisiae* (23) shown as Sc, *Tetrahymena pyriformis* (24) shown as Tp, and *Homo sapiens* (25) shown as Hs. Since the actual 5.8S rRNA sequence was not determined, the termini of the *P. carinii* gene have been chosen based on the known sequence of the homologous gene of *S. cerevisiae*, to which it appears to be closely related. The three nucleotides 5' to the proposed rRNA 5' terminus are shown here in lower case letters. The 5.8S rRNA sequence is 87% identical with the homologous rRNA of *S. cerevisiae*, which was also the species to which *P. carinii* showed closest relatedness of its 16S rRNA gene (3). In contrast, the 5.8S rRNA sequence was 67% and 69% identical with the homologous genes of *T. pyriformis* and *H. sapiens*, respectively.

FIG. 5 shows the sequence of the 26S rRNA gene from FIG. 2 compared to homologous genes from *S. cerevisiae* (26) and *T. pyriformis* (27). The indicated *P. carinii* sequence has an apparent Group I self-splicing intron sequence (see below) omitted after nucleotide 2241, and the *T. pyriformis* sequence has an intron of the same type omitted from a location four nucleotides 3' to the homologous site in the *P. carinii* gene (27). The final 18 nucleotides of the *P. carinii* sequence were determined from organisms from immunosuppressed Hooded rats as shown in FIG. 2. Thus the 26S rRNA genes of both *P. carinii* and *T. pyriformis* have Group I self-splicing introns inserted into the same relatively conserved region. Comparison of the three sequences shown in FIG. 5 indicates the relative conservation of some regions of the 26S rRNA genes, and the greater phylogenetic variability of other regions. The sequence of the coding region of the *P. carinii* 26S rRNA gene shown in FIG. 5 is 83.3% identical with the homologous gene of *S. cerevisiae* and 73.9% identical with that of *T. pyriformis*. Therefore, based upon all three genes (encoding 16S, 5.8S and 26S rRNA) of the major rRNA operon, *P. carinii* appears to be more closely related to *S. cerevisiae* than to representative "protozoa."

Group I Self-splicing Introns of rRNA Genes

As set out in FIG. 2, an apparent Group I self-splicing intron interrupts the 26S rRNA gene sequence in *P. carinii*. This intron is recognizable by the presence of the conserved P, Q, R, and S segments (boldface in FIG. 6A)) present in all introns of this class, as previously reviewed (6–7). There is 74% identity between the sequence of the putative Group I intron in the 26S rRNA gene and that previously reported (5) in the 16S rRNA gene. The entire sequence of the 16S rRNA gene intron in the *P. carinii* isolate has not yet been confirmed, and is identical to that reported (5).

Figure 6A:
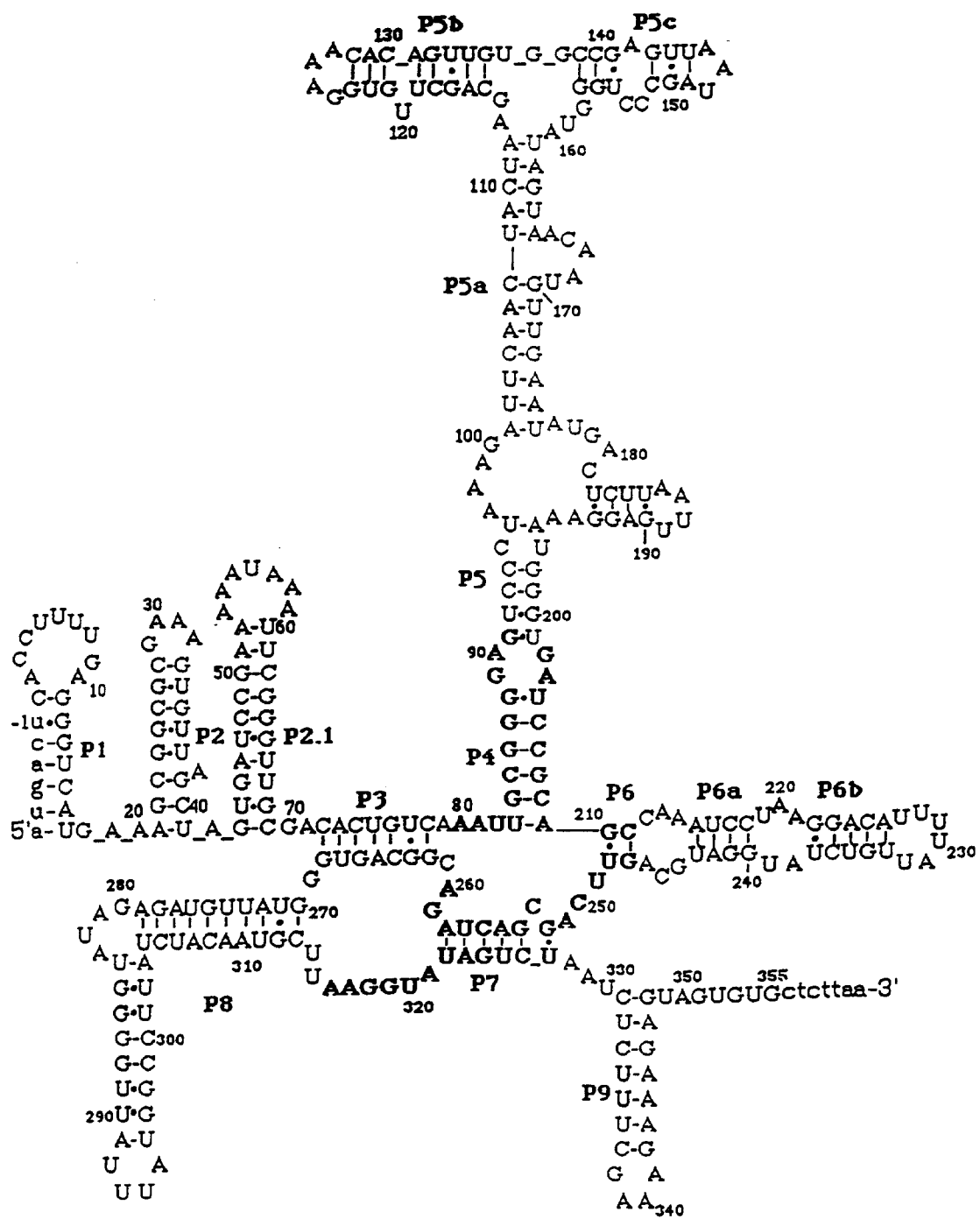
FIG. 6A shows the secondary structure into which the apparent Group I intron in the gene for 26S rRNA of *P. carinii* can be folded. The helices P1–P9 are conserved among Group I introns (6–7). The bases in the intron are numbered 1 through 355, and the flanking exon regions are shown in lower case letters. The consensus sequences P (nucleotides 80–91), Q (nucleotides 202–211), R (nucleotides 247–260) and S (nucleotides 316–327) are shown in boldface.
Figure 6B:
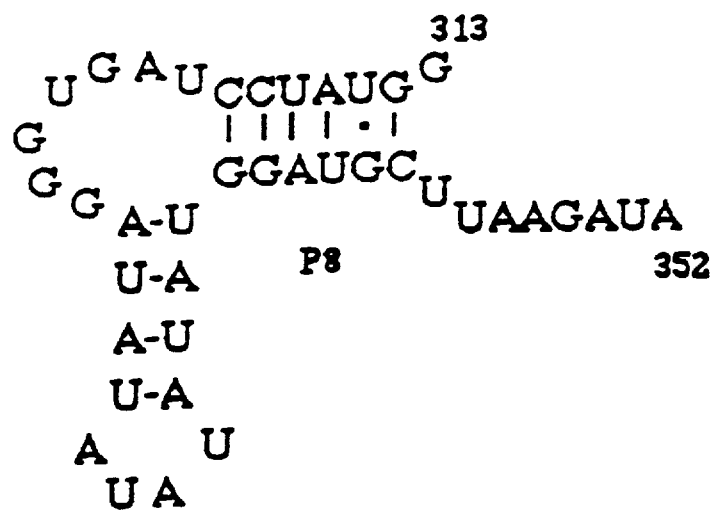
FIG. 6B shows an alternative folding for the P8 helix of the intron (5) in the 16S rRNA gene.

FIG. 6A shows the secondary structure into which the apparent Group I intron in the gene for 26S rRNA of *P. carinii* can be folded. The helices P1-P9 are conserved among Group I introns (6–7). The bases in the intron are numbered 1 through 355, and the flanking exon regions are shown in lower case letters. The consensus sequences P (nucleotides 80–91), Q (nucleotides 202–211), R (nucleotides 247–260) and S (nucleotides 316–327) are shown in boldface. FIG. 6B shows an alternative folding for the P8 helix of the intron (5) in the 16S rRNA gene.

FIG. 6A shows that the 26S rRNA gene intron can be folded into a structure similar to that reported for other Group I self-splicing introns (6–7), including that in the gene encoding 16S rRNA in *P. carinii* (5). This structure is not necessarily the most stable folded structure possible (28), but is most consistent with the consensus folding proposed for Group I introns (7). The structure in FIG. 6A contains the conserved P1 double-helix made up of a pairing of the 5' exon-intron junction with an internal guiding intron sequence (IGS). It also contains an unusually long P8 helix with a bulge-loop on its 5' side. Although the previously proposed structure for the 16S intron (5) does not have such an elongated P8 helix, its structure also can be drawn in this way (FIG. 6B).

PCR primers pairing to the exons on either side of the 26S rRNA gene intron were utilized, including a 5' primer with a 17-nucleotide 5' extension consisting of a bacteriophage SP6 promoter (29), to generate a DNA product consisting of the intron sequence with portions of both flanking exons with an SP6 promoter at the 5' end of the positive strand. Transcription of this DNA by bacteriophage SP6 RNA polymerase (Promega) results in production of RNA catalyzing self-splicing under similar conditions to those reported (5) for self-splicing of the intron in the 16S rRNA gene. Thus the three rRNA genes encoding 16S, 5.8S and 26S rRNA of *P. carinii* closely resemble their homologues in *S. cerevisiae* in sequence. However, they contain Group I self-splicing introns in the 16S and 26S rRNA genes, unlike most known fungi but like some protozoa (27). Group I introns have been found in the 26S rRNA genes of all rat and human derived *P. carinii* but many strains lack the intron in the 16S rRNA gene.

Sequence Variation Between *Pneumocystis carinii* Isolates

In the course of studies to confirm the sequence shown in FIG. 2, various regions of the rRNA operon of *P. carinii* were repeatedly amplified and sequenced. Organisms obtained from the lungs of Sprague-Dawley rats (Sasco) immunosuppressed in isolation chambers yielded the same sequences for duplicate or overlapping amplifications, as summarized in FIG. 1. When portions of the 26S rDNA were amplified, cloned and sequenced from *P. carinii* obtained from Hooded rats immunosuppressed without isolation, they were found to differ in sequence from the same regions obtained from organisms from Sprague-Dawley rats from Sasco (FIGS. 7 and 8).

FIG. 7 shows the sequence of a region of the 26S rRNA gene which was determined for five independent PCR products (summarized in FIG. 1) using three different sets of primers from *P. carinii* from Sprague-Dawley rats, for the region of nucleotides 485–964 as shown in FIG. 5. This sequence is denoted Pc1 in FIG. 7, and was identical in all five determinations, including three derived using PCR primers shown by the underlined sequences in FIG. 7 and two using one primer outside this region and one within it, as shown in the legend of FIG. 7. When the pair of primers shown in FIG. 7 was used to amplify DNA from *P. carinii* from Hooded rats, the sequence shown as Pc2 was obtained. Comparison of these sequences with those of *S. cerevisiae* and *T. pyriformis* 26S rRNA sequences demonstrates that the DNA sequences of the two *P. carinii* isolates differ from each other at multiple positions, with the differences occurring mostly in phylogenetically variable regions of the rRNA sequence. However, the two *P. carinii* sequences are clearly more similar to each other than to the sequence of the *S. cerevisiae* gene, indicating the phylogenetic relatedness of these two isolates.

FIG. 8 shows a comparison of the sequences of the region from nucleotides 2911 through 3327 of the 26S rRNA gene of *P. carinii* (Pc1) from Sprague-Dawley rats (FIG. 5) with the homologous regions from *P. carinii* from Hooded rats (Pc2) and from *S. cerevisiae* (Sc) and *T. pyriformis* (Tp). The fragment denoted Pc1 was amplified using primers 4138 and 4170. The sequence shown for Pc2 was determined based on amplifications using primer pair 4138 and 4139 and pair 4169 and 4170, and ligation-dependent PCR amplification of a fragment extending from oligonucleotide 3427 through a PstI site 381 nucleotides past the 3' end of the 26S rRNA gene. The sequences of homologous regions of the 26S rRNA genes of *S. cerevisiae* (Sc) and *T. pyriformis* (Tp) are shown. The 3'-terminal region of the 26S rRNA gene of *P. carinii* from these two sources differed from each other, with most of the differences in phylogenetically non-conserved regions. Again the two *P. carinii* genes showed greater similarity to each other than to the genes from other species.

When Pc1 DNA template was amplified by PCR using the primer pair 4358 (universal) and 4746 (Pc1-specific), the expected 2,067 bp product was produced. In contrast, no product was generated from Pc2 template with these same primers (FIG. 9). Similarly, primers 4743 (Pc2-specific) and 4744 (Pc2-specific) amplified an approximately 3.0 kbp product from Pc2 template; no similar product was seen with Pc1 template (FIG. 9). Note that in some reaction a barely detectable band of the same size seen with Pc2 template was seen with Pc1 template using the latter primer pair. These data are consistent with Pc1 and Pc2 each containing predominantly genes encoding single distinct major 26S rRNA sequences.

External Transcribed Spacer Sequence

The sequence of the 26S rRNA gene shown in FIG. 3 contains a phylogenetically conserved EcoRI site at position 2875, which is located in a highly conserved region of the sequence. DNA isolated from *P. carinii* from Hooded rats was restricted with pairs of restriction enzymes, including EcoRI and various other "6-cutters," and the resulting fragments were then ligated into pUC18 cut with the same pairs of restriction enzymes. The product of each of the ligation reactions was then subjected to PCR amplification, with thermostable DNA polymerase from *Thermus thermophilus* (Hot Tub, Amersham) using the primer pair: oligonucleotide 3427, which pairs on the positive strand at positions 2911–2931, and oligonucleotide 230, which pairs with a pUC18 region 3' to the polylinker (on the negative strand). When such PCR reactions were analyzed by agarose gel electrophoresis with visualization of bands by ultraviolet light-induced fluorescence in the presence of ethidium bromide, only the pair of restriction enzymes EcoRI and PstI generated a visible DNA band. When this band was cloned and sequenced, its 5' region had the sequence shown as Pc2 in FIG. 8, followed by the final 18 nucleotides of the 26S rRNA gene as shown in FIG. 5 and 381 nucleotides of the following spacer region shown in FIG. 10, which would correspond to the external transcribed spacer region in the homologous operon of most eukaryotes (reviewed in 30). When the same ligation-dependent PCR procedure was followed using the DNA from *P. carinii* from Sprague-Dawley rats, no visible band of DNA was detected. This presumably indicates that the PstI site in the spacer of the DNA denoted Pc2 is absent in Pc1 DNA, and the next one is presumably too distant to support ligation-dependent PCR.

FIG. 10 shows the sequence of the spacer region 3' to the 26S rRNA gene of *P. carinii* from Hooded rats (FIG. 8), which was determined by ligation-dependent PCR. The sequences of Pc2 shown in FIGS. 8 and 10 have been deposited at EMBL/GenBank under accession No. 86759 SEQ ID NO:32 .

In vitro Assay for Drugs Inhibiting Intron Splicing in *Pneumocystis carinii*

Figure 11:
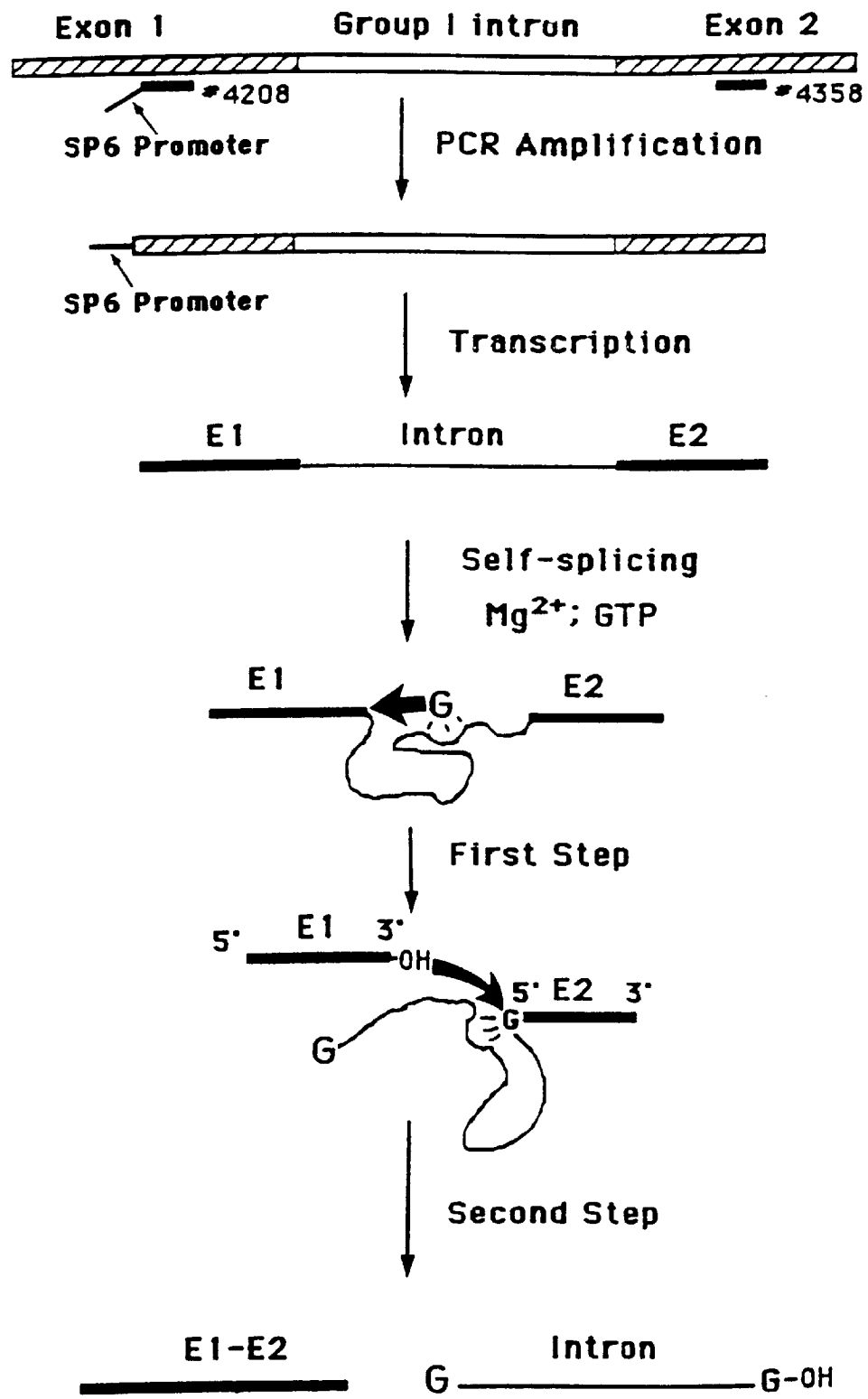
FIG. 11 shows the assay of self-splicing by Group I introns. Polymerase chain reaction (PCR) amplification (56) of the intron from the 26S rRNA gene and a portion of the 5' and 3' flanking exons (660 nucleotides of amplified rRNA gene), between nucleotides 1963 and 2267 of 26S rRNA of isolate Pc1 was performed with primers 4208 (5'-ATTTAGGTGACACTATAGAAGCTATTGGACCAGAC-GGGAAC-3') (SEQ ID NO:33), whose first 17 nucleotides are a bacteriophage SP6 promoter (57), and 4358 (5'-GACGAGGCATTTGGCTACC-3') (SEQ ID NO:35) in a DNA Thermal Cycler (Perkin-Elmer-Cetus), under conditions recommended by the manufacturer. For some experiments a longer PCR product (1296 nucleotides of amplified rRNA gene) was generated by similar methods, using primers 4208 and 3734 (5'-GGGTGAACAATCCAACGCTTACCG-3') to amplify the region between nucleotides 1963 and 2903 of 26S rRNA. Transcription of PCR product DNA (1 µg) by SP6 RNA polymerase to produce E1-I-E2 RNA precursor (1296 or 660 nucleotides in length) was carried out using the Riboprobe System II (Promega) under the recommended conditions.

FIG. 11 shows the assay of self-splicing by Group I introns. Polymerase chain reaction (PCR) amplification (56) of the intron from the 26S rRNA gene and a portion of the 5' and 3' flanking exons (660 nucleotides of amplified rRNA gene), between nucleotides 1963 and 2267 of 26S rRNA of isolate Pc1 was performed with primers 4208 (5'-ATTTAGGTGACACTATAGAAGCTATTGGACCAGAC-GGGAAC-3') (SEQ ID NO:33), whose first 17 nucleotides are a bacteriophage SP6 promoter (57), and 4358 (5'-GACGAGGCATTTGGCTACC-3') (SEQ ID NO:35) in a DNA Thermal Cycler (Perkin-Elmer-Cetus), under conditions recommended by the manufacturer. For some experiments a longer PCR product (1296 nucleotides of amplified rRNA gene) was generated by similar methods, using primers 4208 and 3734 (5'-GGGTGAACAATCCAACGCTTACCG-3') to amplify the region between nucleotides 1963 and 2903 of 26S rRNA. Transcription of PCR product DNA (1 μg) by SP6 RNA polymerase to produce E1-I-E2 RNA precursor (1296 or 660 nucleotides in length) was carried out using the Riboprobe System II (Promega) under the recommended conditions.

FIG. 12 shows the requirement for $Mg^{++}$ for in vitro splicing. Radioactive RNA precursor (1296 nucleotides, 1 nM) was incubated at 37° C. for 30 minutes in the presence of 50 mM Tris-HCl, pH 7.5, 0.4 mM spermidine, 4 units of RNasin, 100 μM GTP and the indicated concentrations of $MgCl_2$ in a volume of 10 μl. Reactions were terminated by addition of 10 μl of 8M urea containing 5 mM Na-EDTA, pH 8.0, and 0.025% each of bromphenol blue and xylene cyanol, followed by heating at 65° C. for 3 minutes and PAGE, with visualization by autoradiography. Lane M contains RNA standards (molecular weights 1.77, 1.52, 1.28, 0.78, 0.53, 0.40, 0.28, and 0.16 kd, BRL), 5'-labeled with $^{32}p$ using bacteriophage T4 polynucleotide kinase (Pharmacia). Lane 1, purified RNA precursor; lane 2, GTP omitted, 5 mM $MgCl_2$; lane 3, no $MgCl_2$, 1 mM EDTA; lanes 4–11, reactions run in the presence of 0, 1, 5, 25, 50, 100, 200 or 500 mM 5 $MgCl_2$, respectively. O indicates origin; P, RNA precursor; I, linear intron; E1-E2, spliced RNA product; C, presumed circularized intron. Bands corresponding to the 5' exon (E1) and G-intron-3' exon (I-E2) are not visible on this exposure.

Figure 13C:
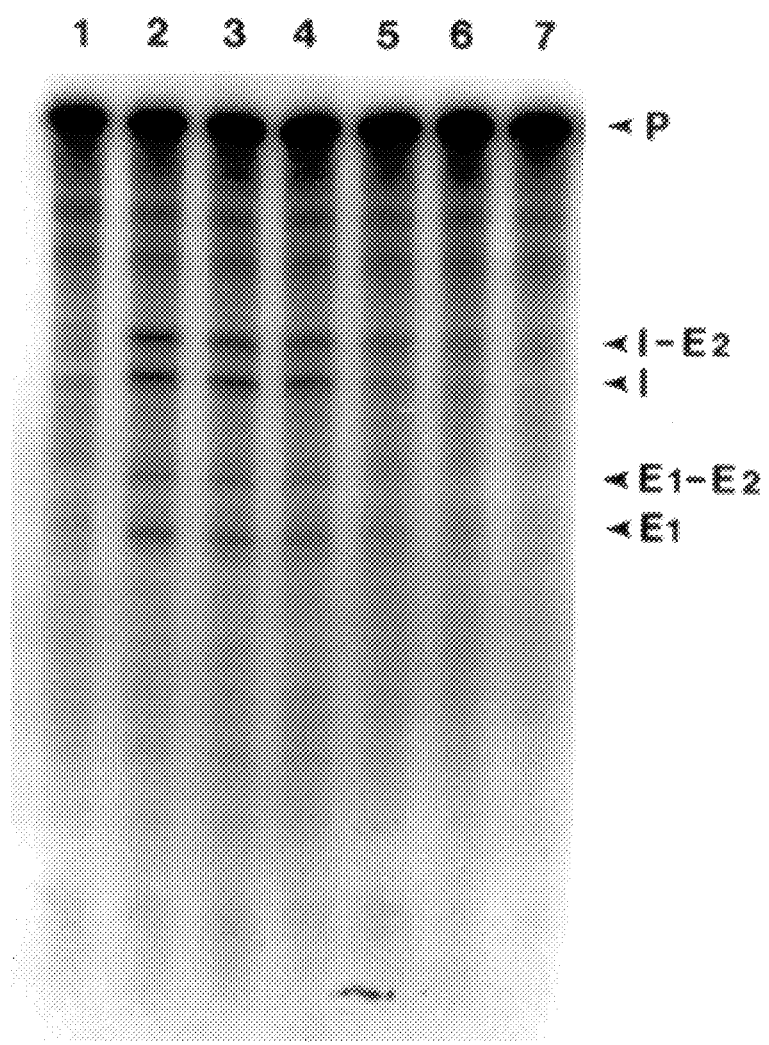

FIGS. 13A through 13D show the inhibition of intron splicing by antibiotics. All experiments were done with 660 nucleotide RNA precursor. In vitro splicing of [$^{32}P$]RNA precursor was performed in the presence of 5 mM MgCl$_2$ and 100 μM GTP (unless otherwise indicated) at 37° C. for 20 minutes as in FIG. 12. Splicing of unpurified transcripts extracted from SP6 RNA polymerase reactions was performed with 12.5 nM of [α-$^{32}$P]GTP replacing non-radioactive GTP (this concentration is below the K$_m$ for GTP which has been determined to be 3 μM). Bands are identified as in FIG. 12. FIG. 13A: Inhibition by gentamicin and tetracycline. Purified [$^{32}$P]RNA precursor splicing was performed as indicated. Lane 1, control without GTP; lane 2, complete reaction without antibiotics; lanes 3–7, gentamicin present at 50, 100, 200, 250 and 500 μM; lanes 8–12, tetracycline present at 10, 50, 100, 200, and 400 μM. FIG. 13B: Inhibition of intron splicing by gentamicin and tetracycline. Splicing of non-radioactive RNA was assayed in the presence of [α-$^{32}$P]GTP with no antibiotic (lanes 1 and 7), with 50, 100, 200, 300, and 500 μM gentamicin (lanes 2–6), and with 50, 100, 200, and 400 μM tetracycline (lanes 8–11). FIG. 13C: Splicing inhibition by ethidium bromide. Reactions of [$^{32}$P]RNA precursor were run in the presence of 10 μM GTP (except lane 1 which contained neither GTP nor ethidium bromide); lanes 2–7, reactions run in the presence of ethidium bromide at 0, 0.5, 1, 5, 10, and 25 μM, respectively. Similar levels of inhibition were observed in reactions run in the presence of 100–500 M GTP. FIG. 13D: Inhibition of splicing by ethidium bromide, as measured by incorporation of [α-$^{32}$P]GTP. Lanes 1–5, reactions run in the presence of 0, 0.5, 1, 5 and 25 μM ethidium bromide, respectively.

Figure 14A:
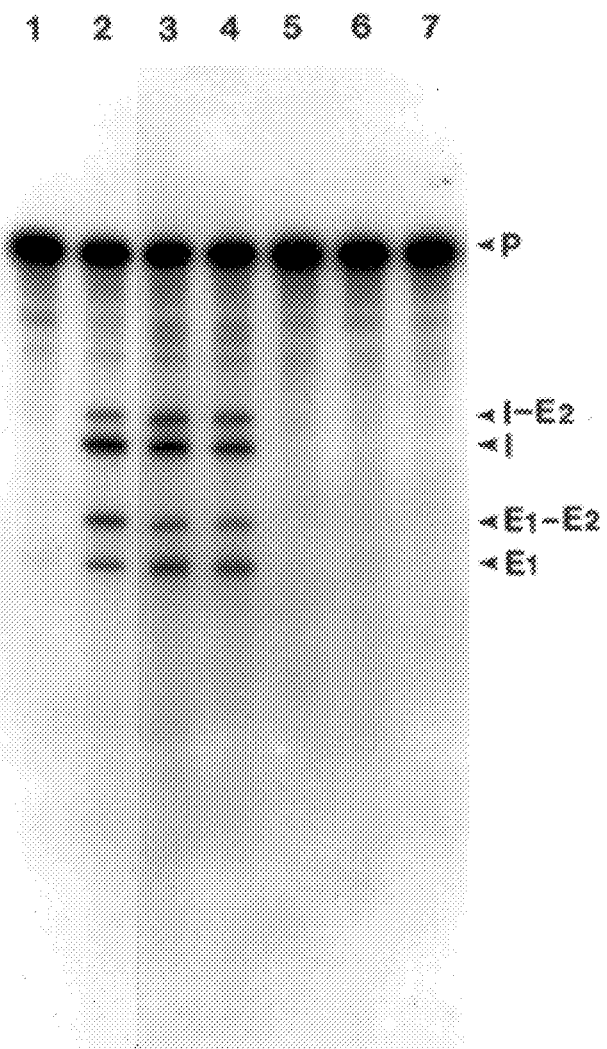
FIGS. 14A and 14B show the inhibition of intron splicing by pentamidine. Reactions were performed as in FIG. 13, with 660 nucleotide RNA precursor.
Figure 14B:
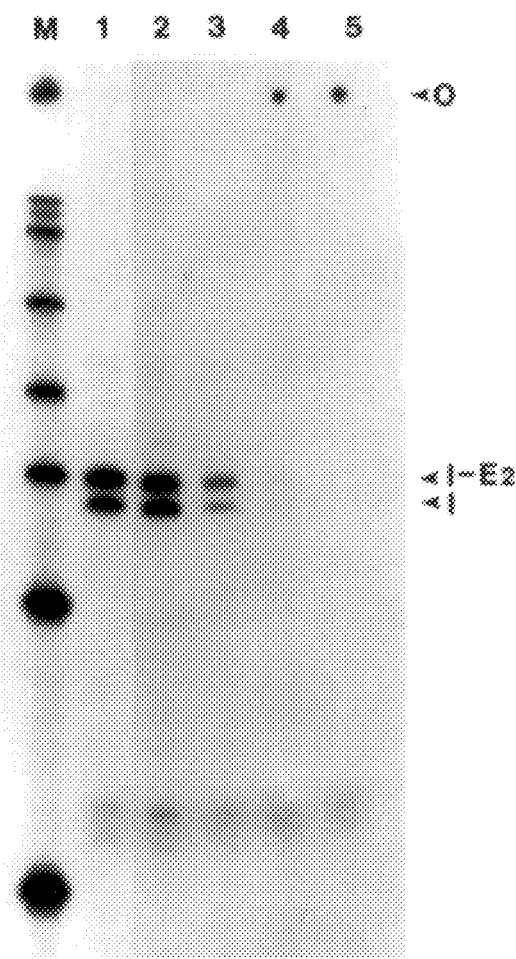

FIGS. 14A and 14B show the inhibition of intron splicing by pentamidine. Reactions were performed as in FIG. 13, with 660 nucleotide RNA precursor. FIG. 14A: Assays of splicing of [$^{32}$P]RNA precursor. Lane 1, reaction run in the absence of GTP; lanes 2–7 contained 0, 180, 200, 250, 300, and 500 μM pentamidine isethionate, respectively. FIG. 14B: Assays of splicing by [α-$^{32}$P]GTP incorporation. Lane M is as described in FIG. 12. Lanes 1–5 contain products of reactions run in the presence of 0, 160, 180, 200, and 250 μM pentamidine isethionate, respectively.

In accord with the present invention, an in vitro method for assaying for an inhibitor of the catalytic Group I self-splicing intron reaction in the nuclear rRNA genes of *Pneumocystis carinii* which comprises the steps of:

(a) providing a DNA template containing the intron (I) from the 26S rRNA gene in *Pneumocystis carinii* and a portion of the 5' and 3' flanking exons (E1 and E2, respectively) between nucleotides 1963 and 2267 of 26S rRNA (660 nucleotides of amplified rRNA gene including the group I intron);

(b) preparing an RNA precursor by transcription of the DNA template in the presence of labeled nucleoside triphosphates to produce a labeled RNA precursor (E1-I-E2);

(c) purifying the RNA precursor;

(d) incubating the RNA precursor and the inhibitor in the presence of guanosine triphosphate and magnesium ions; and (e) determining the degree of inhibition by the inhibitor on the intron splicing reaction in the RNA precursor by measuring the amount of labeled splicing intermediates and splicing products.

In another embodiment, the present invention pertains to an in vitro method for assaying for an inhibitor of the catalytic Group I self-splicing intron reaction in the nuclear rRNA genes of *Pneumocystis carinii* which comprises the steps of:

(a) providing a DNA template containing the intron (I) from the 26S rRNA gene in *Pneumocystis carinii* and a portion of the 5' and 3' flanking exons (E1 and E2, respectively) between nucleotides 1963 and 2267 of 26S rRNA (660 nucleotides of amplified rRNA gene including the group I intron);

(b) preparing an RNA precursor by transcription of the DNA template to produce a RNA precursor (E1-I-E2);

(c) purifying the RNA precursor;

(d) incubating the RNA precursor and the inhibitor in the presence of labeled guanosine triphosphate and magnesium ions; and (e) determining the degree of inhibition by the inhibitor on the intron splicing reaction in the RNA precursor by measuring the amount of labeled splicing intermediates and splicing products.

The present invention is also directed at a method for diagnosing for *Pneumocystis carinii* which comprises detecting the presence of a nucleic acid sequence containing the 26S rRNA gene specific for *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for *Pneumocystis carinii*;

(e) determining whether hybridization in step (d) has occurred.

In another embodiment, the present invention pertains to a method for diagnosing for a species of *Pneumocystis carinii* which comprises detecting the presence of a nucleic acid sequence containing the 26S rRNA gene specific for that species of *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 26S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 26S rRNA gene specific for that species of *Pneumocystis carinii*;

(e) determining whether hybridization in step (d) has occurred.

In yet another embodiment, the present invention pertains to a method for diagnosing for a species of *Pneumocystis carinii* which comprises detecting the presence of a nucleic acid sequence containing the 16S rRNA gene specific for that species of *Pneumocystis carinii* in a sample which comprises the steps of:

(a) treating the sample with an oligodeoxyribonucleotide primer for each strand of the nucleic acid sequence, four different nucleoside triphosphates, and an agent for polymerization under hybridizing conditions, such that for each strand an extension product of each primer is synthesized which is sufficiently complementary to each strand of the nucleic acid sequence being detected to hybridize therewith and contains the 16S rRNA gene specific for that species of *Pneumocystis carinii*, wherein the primers are selected such that the extension product synthesized from one primer, when it is separated from its complement, can serve as a template for synthesis of the extension product of the other primer;

(b) treating the sample from step (a) under denaturing conditions to separate the primer extension products from the templates on which they are synthesized if the sequence to be detected is present;

(c) treating the product from step (b) with oligodeoxyribonucleotide primers, four different nucleoside triphosphates, and an agent for polymerization such that a primer extension product is synthesized using each of the single strands produced in step (b) as a template, resulting in amplification of the sequence to be detected if present;

(d) hybridizing the primer extension products from step (c) with a labeled oligodeoxyribonucleotide probe complementary to the 16S rRNA gene specific for that species of *Pneumocystis carinii*;

(e) determining whether hybridization in step (d) has occurred.

Amplified products may be detected by electrophoresis on agarose gels followed by hybridization with a radioactive or nonradioactive probe consisting of a third oligonucleotide specific for a sequence lying between two PCR primers on the *P. carinii* gene. The method may further comprise in steps (d) and (e) a positive control which contains the 26S rRNA gene specific for *Pneumocystis carinii* and a negative control which does not contain the 26S rRNA gene.

This invention also provides a method for diagnosing for various species of *P. carinii* by detecting the presence of a nucleic acid sequence containing the particular 16S or 26S rRNA gene sequence specific for that species of *P. carinii*. Specific PCR primers and hybridization probes for specific subtypes of *P. carinii* may be employed based on sequence analysis of different subtypes found in infected rats. Alternatively, single pairs of PCR primers based on sequences shared by all isolates may be used for strain identification if the distances between sequences shared by different isolates are distinct. This latter approach may prove useful if different strains differ in the location of the intron in their genes.

Methods for amplifying and detecting nucleic acid sequences are described in detail in U.S. Pat. Nos. 4,683,195, 4,683,202, and 4,965,188, which disclosures are incorporated herein by reference.

Appendium of References

1. Pifer, L. L., Hughes, W. T., Stagno, S., and Woods, D. (1978) Pediatrics, 61, 35–41.
2. Hughes, W. T. (1991) *Annu. Rev. Med.*, 42, 287–295.
3. Edman, J. C., Kovacs, J. A., Masur, H., Santi, D. V., Elwood, H. J., and Sogin, M. L. (1988) *Nature*, 334, 519–522.
4. Stringer, S. L., Stringer, J. R., Blase, M. A., Walzer, P.D., and Cushion, M.T. (1989) *Exptal. Parasitol.*, 68, 450–461.
5. Sogin, M. L., and Edman, J. C. (1989) *Nucleic Acids Res.*, 17, 5349–5359.
6. Cech, T. R. (1990) *Annu. Rev. Biochem.*, 59, 543–568.
7. Cech, T. R. (1988) *Gene*, 73, 259–271.
8. Watanabe, J., Hori, H., Tanabe, K., and Nakamura, Y. (1989) *Mol. Biochem. Parasitol.*, 32, 163–168.
9. Halanych, K. M. (1991) *Mol. Biol. Evol*, 8, 249–253.
10. Warner, J. (1989) *MicrobioL Rev.*, 53, 256–271.
11. Yonagathan, T., Lin, H., and Buck, G. A. (1989). *Molec. Microbiol.*, 3, 1473–1480.
12. Lundgren, B., Cotton, R., Lundgren, J. D., Edman, J. C., and Kovacs, J. A. (1990) *Infect. Immun.*, 58, 1705–1710.
13. Kitada, K., Oka,S., Kimura, S., Shimada, K., Serikawa, T., Yamada, J., Tsunoo, H., Egawa, K., and Nakamura, Y. (1991) *J. Clin. Microbiol*, 29, 1985–1990.
14. Sinclair, K., Wakefield, A. E., Banerji, S., and Hopidn, J. M. (1991) *Mol. Biochem. Parasitol.*, 45, 183–184.
15. Radding, J. A., Armstrong, M. Y. K., Ullu, E., and Richards, F. F. (1989) *Infect. Immun.*, 57, 2149–2157.
16. Witebsky, F. G., Andrews, J. W. B., Gill, V. J., and MacLowry, J. D. (1988) *J. Clin. Microbiol.*, 26, 774–775.
17. Edman, U., Edman, J. C., Lundgren, B., and Santi, D. V. (1989) *Proc. Natl. Acad. Sci. USA*, 86, 6503–6507.
18. Edman, J. C., Edman, U., Cao, M., Lundgren, B., Kovacs, J. A., and Santi, D.V. (1989) *Proc. Natl. Acad. Sci. USA*, 86, 8625–8629.
19. Sambrook, J., Fritsch, E. F., and Maniatis, T. (1989) *Molecular Cloning: A Laboratory Manual*, Second Edition. Cold Spring Harbor Laboratory Press. Cold Spring Harbor.
20. Torczynski, R. M., Fuke, M., and Bollon, A. P. (1985) *DNA*, 4, 282–291.
21. Jones, M. D., and Foulkes, N. S. (1989) *Nucleic Acids Res.*, 17, 8387–8388.
22. Zhou, Y., Zhang, X., and Ebright, R. H. (1991) *Nucleic Acids Res.*, 19, 6052.
23. Bell, G. I., Degennaro, L. J., Gelfand, D. H., Bishop, R. J., Valenzuela, P., and Rutter, W. J. (1977) *J. Biol. Chem.*, 252, 8118–8125.

24. Fujiwara, H., and Ishikawa, H. (1982) *Nucleic Acids Res.*, 10, 5173–5182.
25. Nazar, R. N., Sitz, T. O., and Busch, H. (1976) *Biochemistry*, 15, 505–508.
26. Georgiev, O. I., Nikolaev, N., and Hadjiolov, A. A. (1981) *Nucleic Acids Res.*, 9, 6953–6958.
27. Nielsen, H., and Engberg, J. (1985) *Nucleic Acids Res.*, 13, 7445–7455.
28. Zuker, M., and Stiegler, P. (1981) *Nucleic Acids Res.*, 9, 133–148.
29. Nam, S. C., and Kang, C. (1988) *J. Biol. Chem.*, 263, 18123–18127.
30. Musters, W., Planta, R. J., van Heerikhuizen, H., and Raué (1990) in Hill, W. E., Dahlberg, A., Garrett, R. A., Moore, P. B., Schlessinger, D., and Warner, J. R. (eds.), *The Ribosome*, Amer. Soc. Microbiol., New York, pp. 435–442.
31. van Ahsen, U., Davies, J., and Schroeder, R. (1991) *Nature*, 353, 368–370.
32. Vossbrinck, C. R., Maddox, J. V., Friedman, S., Debrunner-Vossbrinck, P. A., and Woese, C. R. (1987) *Nature*, 326, 411–414.
33. Kim, H. K., Hughes, W. T., and Feldman, S. (1972) *Proc. Soc. Exptal. Biol. Med.*, 142, 304–309.
34. Walzer, P. D., and Rutledge, M. E. (1980) *J. Infect. Dis.*, 142, 449.
35. Gigliotti, F., Stokes, D. C., Cheatham, A. B., Davis, D. S., and Hughes, W. T. (1986) *J. Infect. Dis.*, 154, 315–322.
36. Link, M. J., Cushion, M. T., and Walzer, P. D. (1989) *Infect. Immun.*, 57, 1547–1555.
37. Tanabe, K., Fuchimoto, M., Egawa, K., and Nakamura, Y. (1988) *J. Infect. Dis.*, 157, 593–596.
38. Hughes, W. T., and Gigliotti, F. (1988) *J. Infect. Dis.*, 157, 432–433.
39. Gunderson, J. J., Sogin, M. L., Wollett, G., Hollingdale, M., de la Cruz, V. F., Waters, A. P., and McCutchan, T. F. (1987) *Science*, 238, 933–937.
40. Gonzalez, I. L., Gorski, J. L., Campen, T. J., Dorney, D. J., Erickson, J. M., Sylvester, J. E., and Schmickel, R. D. (1985) *Proc. Natl. Acad. Sci. USA*, 82, 7666–7670.
41. van Keulen, H., Campbell, S. L., Erlandsen, S. L., and Jarroll, E. L. (1991) *Mol. Biochem. ParasitoL*, 46, 275–284.
42. Pifer, L. L., Hughes, W. T., Stagno, S. & Woods, D. Pediatrics 61, 35–41 (1978).
43. Smulian, A. G. & Walzer, P. D. Crit. Revs. Microbiol. 18, 191–216 (1992).
44. Edman, J. C., Kovacs, J. A., Masur, H., Santi, D. V., Elwood, H. J. & Sogin, M. L. Nature 334, 519–522 (1988).
45. Sogin, M. L. & Edman, J. C. Nucleic Acids Res. 17, 5349–5359 (1989).
46. Stringer, S. L., Stringer, J. R., Blase, M. A., Walzer, P. D. & Cushion, M. T. Exp. Parasitol. 68, 450–461 (1989).
47. Hughes, W. T. Annu. Rev. Med. 42, 287–295 (1991).
48. Ivády, G. & Páldy, L. Monatsschr. Kinderheilkd. 106, 10–14 (1957).
49. Tidwell, R. R., Jones, S. K., Geratz, J. D., Ohemeng, K. A., Cory, M. & Hall, J. E. J. Med. Chem. 33, 1252–1257 (1990).
50. Tidwell, R. R., Jones, S. K., Geratz, J. D., Ohemeng, K. A., Bell, C. A., Berger, B. J. & Hall, J. E. Ann. N. Y. Acad. Sci. 616, 421–441 (1990).
51. Cory, M., Tidwell, R. R. & Fairley, T. A. J. Med. Chem. 35, 431–438 (1992).
52. Dykstra, C. C. & Tidwell, R. R. J. Protozool. 38, 78S–81S (1991).
53. Dujon, B. Gene 82, 91–114 (1989).
54. Cech, T. R. Annu. Rev. Biochem. 59, 543–568 (1990).
55. von Ahsen, U., Davies, J. & Schroeder, R. Nature 353, 368–370 (1991).
56. Salki, R. K., Scharf, S., Faloona, F., Mullis, K. B., Horn, G. T., Erlich, H. A. & Armnheim, N. Science 230, 1350–1354 (1985).
57. Nam, S.-C. & Kang, C. J. Biol. Chem. 263, 18123–18127 (1988).
58. Zaug, A. J., Grabowski, P. J. & Cech, T. R. Nature 301, 578–583 (1983).
59. Ehrenman, K., Pedersen-Lane, J., West, D., Herman, R., Maley, F. & Belfort, M. Proc. Natl. Acad. Sci. U.S.A. 83, 5875–5879 (1986).
60. Tabak, H. F., Van der Horst, G., Kamps, A. M. J. E. & Arnberg, A. C. Cell 48, 101–110 (1987).
61. von Ahsen, U. & Schroeder, R. Nucleic Acids Res. 19, 2261–2265 (1991).
62. Michel, F., Hanna, M., Green, R., Bartel, D. P. & Szostak, J. W. Nature 342, 391–395 (1989).
63. Herschlag, D. Biochemistry 31, 1386–1394 (1992).
64. Hatfield, C., Kasarskis, A. & Staben, C. J. Protozool. 38, 70S–71S (1991).
65. Liu, Y., Rocourt, M., Pan, S., Liu, C., and Leibowitz, M.J. Nucleic Acids Res. 20, 3763–3772 (1992).

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

We claim:

1. An in vitro method for assaying for an inhibitor of the catalytic Group I self-splicing intron reaction in the nuclear rRNA genes of *Pneumocystis carinii* which comprises the steps of:

(a) providing a DNA template containing the intron (I) from the 26S rRNA gene in *Pneumocystis carinii* and a portion of the 5' and 3' flanking exons, E1 and E2, respectively, between nucleotides 1963 and 2267 of 26S rRNA, 660 nucleotides of amplified rRNA gene including the group I intron;

(b) preparing an RNA precursor by transcription of the DNA template in the presence of labeled nucleoside triphosphates to produce a labeled RNA precursor;

(c) purifying the RNA precursor;

(d) incubating the RNA precursor and the inhibitor in the presence of guanosine triphosphate and magnesium ions; and (e) determining the degree of inhibition by the inhibitor on the intron splicing reaction in the RNA precursor by measuring the amount of labeled splicing intermediates and splicing products.

2. The method according to claim 1, wherein the DNA template in step (a) is prepared by polymerase chain reaction amplification of the intron from the 26S rRNA gene and the portion of the 5' and 3' flanking exons between nucleotides 1963 and 2267 of 26S rRNA, wherein the amplification results in synthesis of a product of 660 nucleotides of amplified rRNA gene.

3. The method according to claim 1, wherein the DNA template in step (a) is prepared by polymerase chain reaction amplification of a precursor-RNA-derived cDNA with two oligodeoxyribonucleotide primers, wherein one primer is collinear with the 5' terminus of the RNA precursor and has a 17-nucleotide extension on its terminus consisting of the positive strand of a consensus bacteriophage SP6 promoter and the other primer is collinear with the inverse complement of the 3' terminus of the RNA precursor.

4. The method according to claim 3, wherein the two oligodeoxyribonucleotide primers are 4208 (5'-ATTTAGGTGACACTATAGAAGCTATTGGACCAGAC-GGGAAC-3') (SEQ ID NO:33), in which the first 17 nucleotides are a bacteriophage SP6 promoter, and 4358 (5'-GACGAGGCATTTGGCTACC-3') (SEQ ID NO:34) to amplify the region between nucleotides 1963 and 2267 of 26S rRNA.

5. The method according to claim 4, wherein the two oligodeoxyribonucleotide primers are 4208 (5'-ATTTAGGTGACACTATAGAAGCTATTGGACCAGAC-GGGAAC-3') (SEQ ID NO:33) and 3734 (5'-GGGTGAACAATCCAACGCTTACCG-3') (SEQ ID NO:35) to amplify the region between nucleotides 1963 and 2903 of 26S rRNA.

6. The method according to claim 1, wherein the DNA template in step (a) is a recombinant DNA plasmid linearized by cleavage with a suitable restriction enzyme.

7. The method according to claim 1, wherein the RNA precursor in step (b) is prepared by transcription of the DNA template by SP6 RNA polymerase.

8. The method according to claim 1, wherein the labeled nucleoside triphosphate, in step (b) are [$\alpha$-$^{32}$P]guanosine triphosphate or [$\alpha$-$^{32}$P]uridine triphosphate.

9. The method according to claim 1, wherein the RNA precursor in step (c) is purified by polyacrylamide gel electrophoresis.

10. An in vitro method for assaying for an inhibitor of the catalytic Group I self-splicing intron reaction in the nuclear rRNA genes of *Pneumocystis carinii* which comprises the steps of:

(a) providing a DNA template containing the intron (I) from the 26S rRNA gene in *Pneumocystis carinii* and a portion of the 5' and 3' flanking exons, E1 and E2, respectively between nucleotides 1963 and 2267 of 26S rRNA, 660 nucleotides of amplified rRNA gene including the group I intron;

(b) preparing an RNA precursor by transcription of the DNA template to produce a RNA precursor;

(c) purifying the RNA precursor;

(d) incubating the RNA precursor and the inhibitor in the presence of labeled guanosine triphosphate and magnesium ions; and (e) determining the degree of inhibition by the inhibitor on the intron splicing reaction in the RNA precursor by measuring the amount of labeled splicing intermediates and splicing products.

11. The method according to claim 10, wherein the DNA template in step (a) is prepared by polymerase chain reaction amplification of the intron from the 26S rRNA gene and the portion of the 5' and 3' flanking exons between nucleotides 1963 and 2267 of 26S rRNA, wherein the amplification results in synthesis of a product of 660 nucleotides of amplified rRNA gene.

12. The method according to claim 11, wherein the DNA template in step (a) is prepared by polymerase chain reaction amplification of a precursor-RNA-derived cDNA with two oligodeoxyribonucleotide primers, wherein one primer is collinear with the 5' terminus of the RNA precursor and has a 17-nucleotide extension on its terminus consisting of the positive strand of a consensus bacteriophage SP6 promoter and the other primer is collinear with the inverse complement of the 3' terminus of the RNA precursor.

13. The method according to claim 14, wherein the two oligodeoxyribonucleotide primers are 4208 (5'-ATTTAGGTGACACTATAGAAGCTATTGGACCAGA-CGGGAAC-3') (SEQ ID NO:33), in which the first 17 nucleotides are a bacteriophage SP6 promoter, and 4358 (5'-GACGAGGCATTTGGCTACC-3') (SEQ ID NO:34) to amplify the region between nucleotides 1963 and 2267 of 26S rRNA.

14. The method according to claim 14, wherein the two oligodeoxyribonucleotide primers are 4208 (5'-ATTTAGGTGACACTATAGAAGCTATTGGACCAGA-CGGGAAC-3') (SEQ ID NO:33) and 3734 (5'-GGGTGAACAATCCAACGCTTACCG-3') (SEQ ID NO:35) to amplify the region between nucleotides 1963 and 2903 of 26S rRNA.

15. The method according to claim 10, wherein the DNA template in step (a) is a recombinant DNA plasmid linearized by cleavage with a suitable restriction enzyme.

16. The method according to claim 10, wherein the RNA precursor in step (b) is prepared by transcription of the DNA template by SP6 RNA polymerase.

17. The method according to claim 10, wherein the RNA precursor in step (c) is purified by polyacrylamide gel electrophoresis.

18. The method according to claim 10, wherein the labeled guanosine triphosphate in step (d) is [$\alpha$-$^{32}$P] guanosine triphosphate.

* * * * *